US012664644B2

(12) United States Patent
Gorton et al.

(10) Patent No.:  US 12,664,644 B2
(45) Date of Patent:       Jun. 23, 2026

(54) SYSTEMS AND METHODS FOR PROCESSING ELECTRONIC IMAGES TO VISUALIZE COMBINATIONS OF SEMANTIC PATHOLOGY FEATURES

(71) Applicant: PAIGE.AI, Inc., New York, NY (US)

(72) Inventors: Danielle Gorton, Beacon, NY (US); Christopher Kanan, Pittsford, NY (US); Patricia Raciti, New York, NY (US)

(73) Assignee: Paige.AI, Inc., New York, NY (US)

( * ) Notice: Subject to any disclaimer, the term of this patent is extended or adjusted under 35 U.S.C. 154(b) by 538 days.

(21) Appl. No.: 18/062,677

(22) Filed: Dec. 7, 2022

(65) Prior Publication Data

US 2023/0177685 A1      Jun. 8, 2023

Related U.S. Application Data

(60) Provisional application No. 63/286,604, filed on Dec. 7, 2021.

(51) Int. Cl.
| | |
|---|---|
| *G06K 9/00* | (2022.01) |
| *G06F 3/04817* | (2022.01) |
| *G06F 3/14* | (2006.01) |
| *G06T 7/00* | (2017.01) |
| *G06V 10/74* | (2022.01) |
| *G16H 30/40* | (2018.01) |

(52) U.S. Cl.
CPC ........ *G06T 7/0012* (2013.01); *G06F 3/04817* (2013.01); *G06F 3/14* (2013.01); *G06V*

*10/761* (2022.01); *G16H 30/40* (2018.01); *G06T 2207/30024* (2013.01)

(58) Field of Classification Search
None
See application file for complete search history.

(56) References Cited

U.S. PATENT DOCUMENTS

| | | | |
|---|---|---|---|
| 2020/0294231 A1 | 9/2020 | Tosun et al. | |
| 2020/0388029 A1* | 12/2020 | Saltz .................... | G06V 10/267 |
| 2023/0035298 A1* | 2/2023 | Tward ..................... | C12N 9/22 |

FOREIGN PATENT DOCUMENTS

| | | |
|---|---|---|
| WO | 2021138087 A1 | 7/2021 |
| WO | 2021226382 A1 | 11/2021 |

* cited by examiner

*Primary Examiner* — Wei Wen Yang
(74) *Attorney, Agent, or Firm* — Bookoff McAndrews, PLLC

(57)      ABSTRACT

Aspects disclosed herein may provide a computer-implemented method for processing electronic medical images. The method may include receiving one or more digital images of a pathology specimen, detecting a presence of one or more incidents of one or more attributes in the received digital image, detecting a spatial relationship of the one or more incidents, selecting, based on the detected spatial relationship, one or more incidents of the one or more attributes, and outputting, to a display, a visual depiction of the one or more selected incidents and the spatial relationship.

18 Claims, 18 Drawing Sheets

200

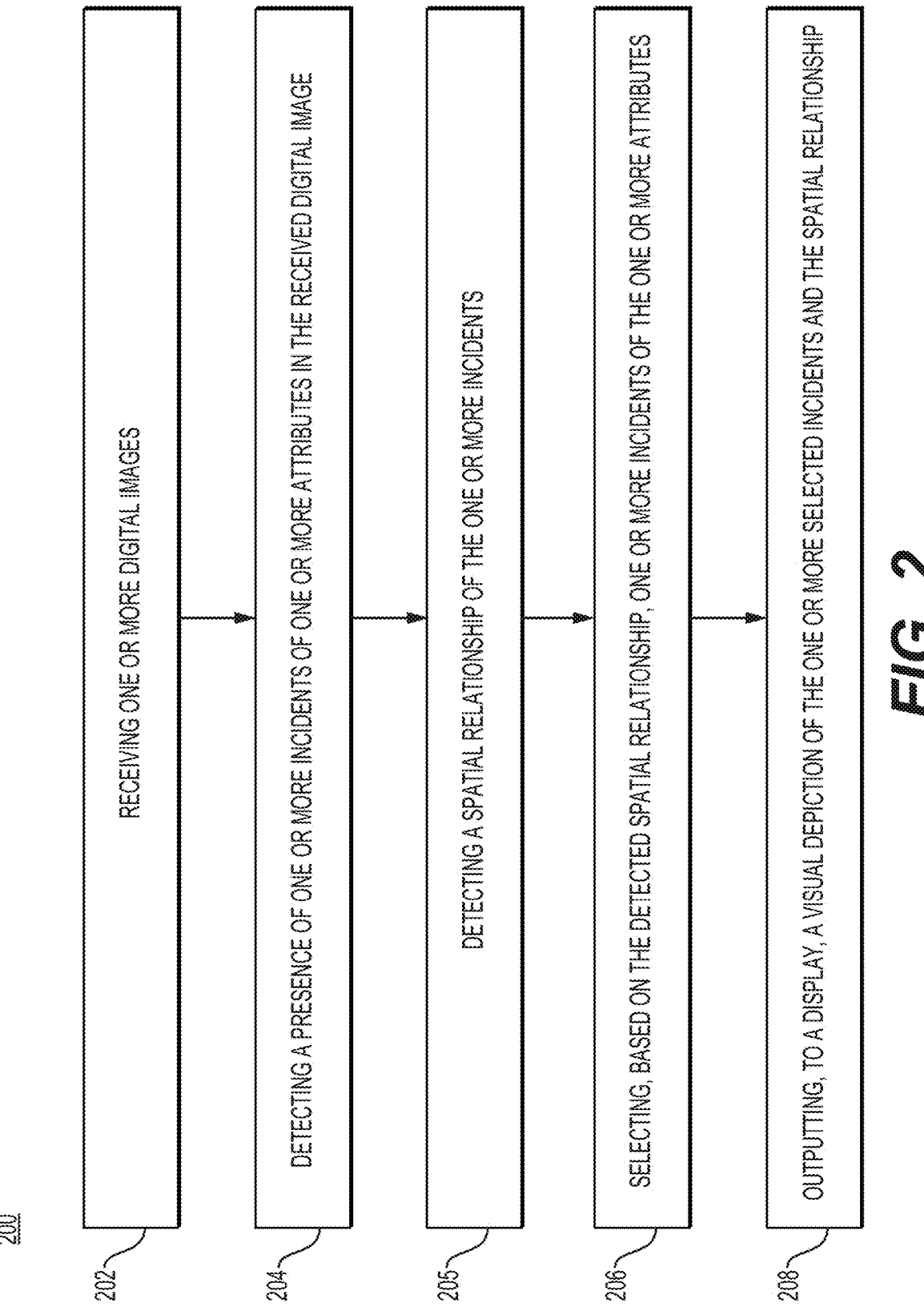

200

202 RECEIVING ONE OR MORE DIGITAL IMAGES

204 DETECTING A PRESENCE OF ONE OR MORE INCIDENTS OF ONE OR MORE ATTRIBUTES IN THE RECEIVED DIGITAL IMAGE

205 DETECTING A SPATIAL RELATIONSHIP OF THE ONE OR MORE INCIDENTS

206 SELECTING, BASED ON THE DETECTED SPATIAL RELATIONSHIP, ONE OR MORE INCIDENTS OF THE ONE OR MORE ATTRIBUTES

208 OUTPUTTING, TO A DISPLAY, A VISUAL DEPICTION OF THE ONE OR MORE SELECTED INCIDENTS AND THE SPATIAL RELATIONSHIP

FIG. 2

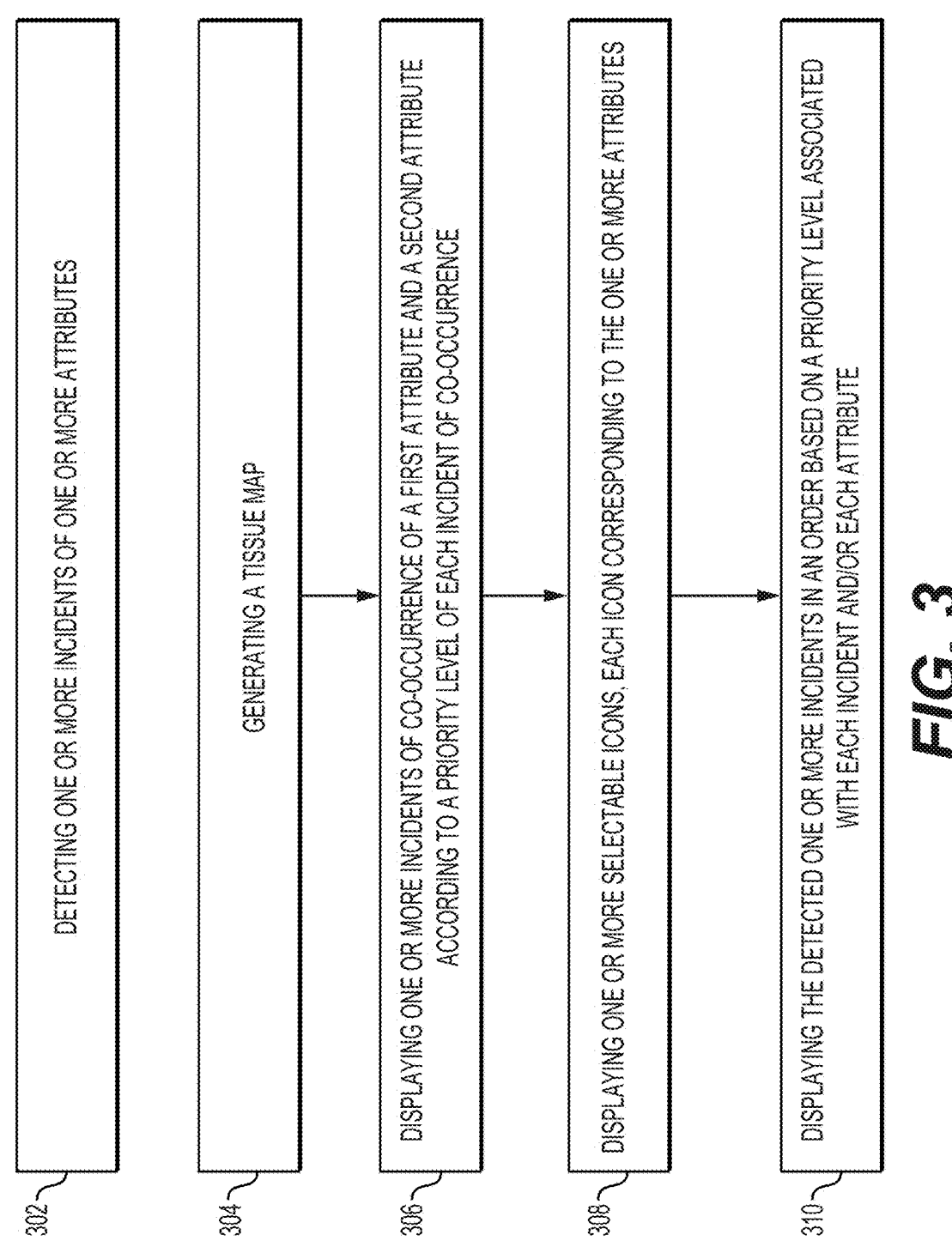

300

302  DETECTING ONE OR MORE INCIDENTS OF ONE OR MORE ATTRIBUTES

304  GENERATING A TISSUE MAP

306  DISPLAYING ONE OR MORE INCIDENTS OF CO-OCCURRENCE OF A FIRST ATTRIBUTE AND A SECOND ATTRIBUTE ACCORDING TO A PRIORITY LEVEL OF EACH INCIDENT OF CO-OCCURRENCE

308  DISPLAYING ONE OR MORE SELECTABLE ICONS, EACH ICON CORRESPONDING TO THE ONE OR MORE ATTRIBUTES

310  DISPLAYING THE DETECTED ONE OR MORE INCIDENTS IN AN ORDER BASED ON A PRIORITY LEVEL ASSOCIATED WITH EACH INCIDENT AND/OR EACH ATTRIBUTE

FIG. 3

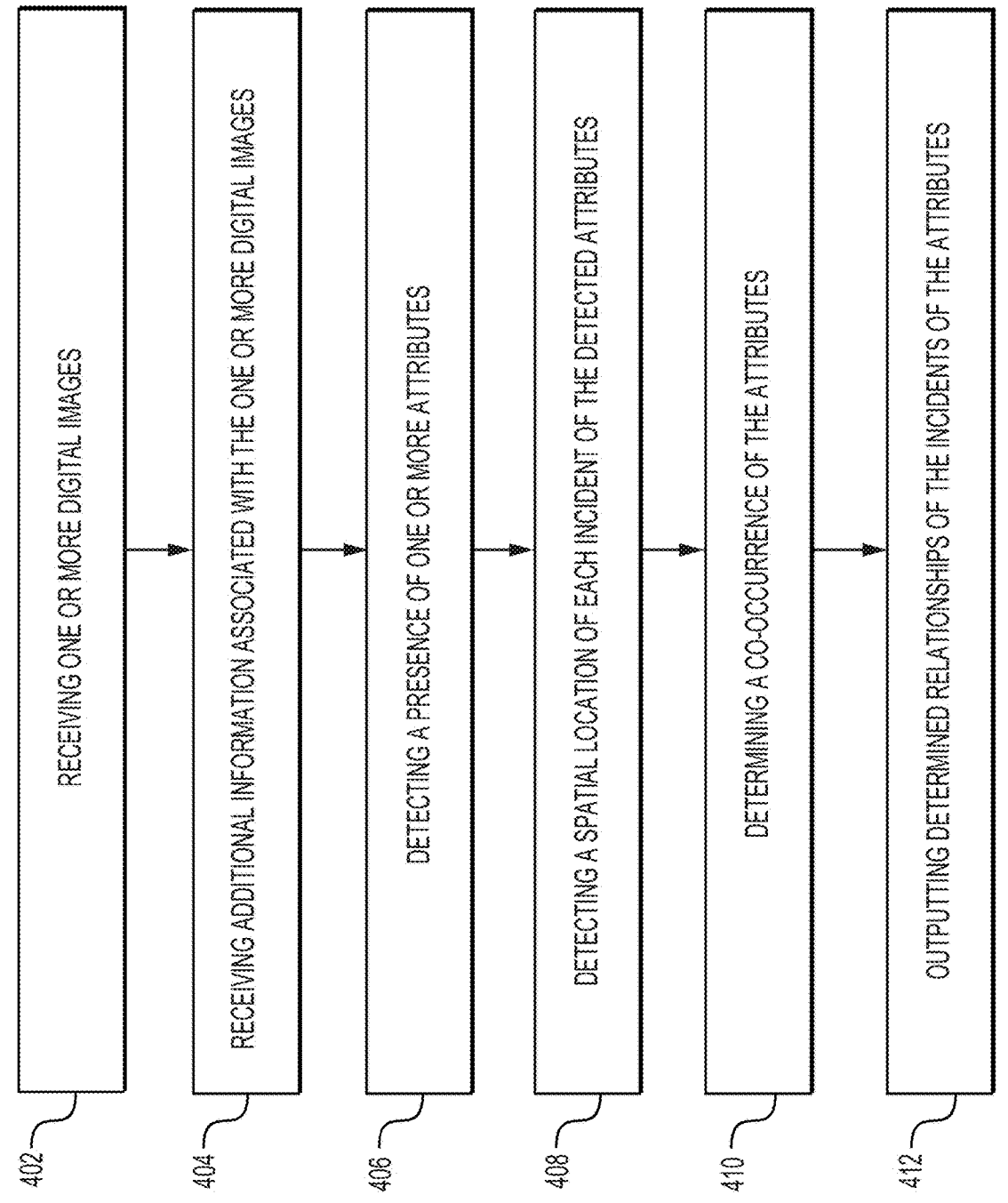

400

402 RECEIVING ONE OR MORE DIGITAL IMAGES

404 RECEIVING ADDITIONAL INFORMATION ASSOCIATED WITH THE ONE OR MORE DIGITAL IMAGES

406 DETECTING A PRESENCE OF ONE OR MORE ATTRIBUTES

408 DETECTING A SPATIAL LOCATION OF EACH INCIDENT OF THE DETECTED ATTRIBUTES

410 DETERMINING A CO-OCCURRENCE OF THE ATTRIBUTES

412 OUTPUTTING DETERMINED RELATIONSHIPS OF THE INCIDENTS OF THE ATTRIBUTES

502 — RECEIVING SPATIAL LOCATIONS AND/OR DETERMINED CO-OCCURRENCES OF ATTRIBUTES

504 — RECEIVING ADDITIONAL INFORMATION ASSOCIATED WITH THE ATTRIBUTES

506 — APPLYING ONE OR MORE POLICIES TO DETERMINE ONE OR MORE DISPLAYS

508 — OUTPUTTING THE ONE OR MORE DETERMINED DISPLAYS

500

502 — RECEIVING SPATIAL LOCATIONS AND/OR DETERMINED CO-OCCURRENCES OF ATTRIBUTES

504 — RECEIVING ADDITIONAL INFORMATION ASSOCIATED WITH THE ATTRIBUTES

518 — RANKING THE ATTRIBUTES AND/OR THE CO-OCCURRENCES OF ATTRIBUTES

520 — OUTPUTTING ONE OR MORE DISPLAYS SHOWING THE ATTRIBUTES BASED ON THE RANKING

600

602 RECEIVING ONE OR MORE DIGITAL IMAGES FROM A SAMPLE

604 RECEIVING ADDITIONAL INFORMATION ASSOCIATED WITH THE ONE OR MORE DIGITAL IMAGES

606 DETECTING A PRESENCE AND LOCATION OF ONE OR MORE FIRST INCIDENTS OF A FIRST ATTRIBUTE

608 DETECTING A PRESENCE AND LOCATION OF ONE OR MORE SECOND INCIDENTS OF A SECOND ATTRIBUTE

610 COMPARING THE DETECTED LOCATIONS OF THE ONE OR MORE FIRST INCIDENTS AND THE SECOND INCIDENTS

612 DETERMINING A DISEASE STATE BASED ON THE COMPARISON

614 OUTPUTTING THE FIRST AND/OR SECOND ATTRIBUTES ON A DISPLAY

FIG. 6

700

702 RECEIVING ONE OR MORE DIGITAL IMAGES FROM A SAMPLE

704 RECEIVING ADDITIONAL INFORMATION ASSOCIATED WITH THE ONE OR MORE DIGITAL IMAGES

706 DETECTING A PRESENCE AND LOCATION OF A PREDETERMINED MUSCLE

708 DETECTING A PRESENCE AND LOCATION OF AN INVASION

710 COMPARING THE DETECTED LOCATION OF THE PREDETERMINED MUSCLE AND THE INVASION

712 DETERMINING A DISEASE STATE BASED ON THE COMPARISON

714 OUTPUTTING A DISPLAY OF THE INVASION AND THE PREDETERMINED MUSCLE

*FIG. 7*

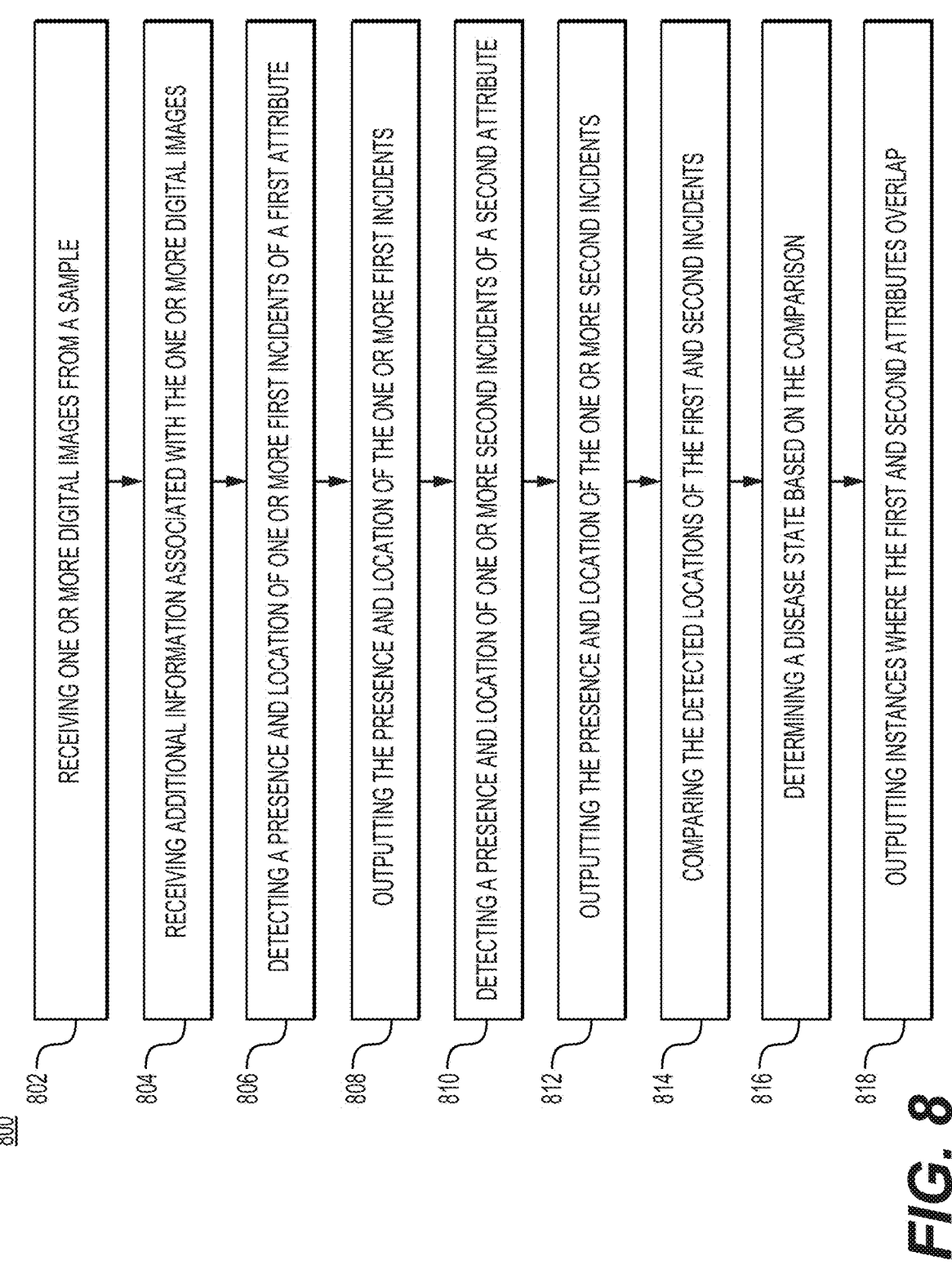

800

802 RECEIVING ONE OR MORE DIGITAL IMAGES FROM A SAMPLE

804 RECEIVING ADDITIONAL INFORMATION ASSOCIATED WITH THE ONE OR MORE DIGITAL IMAGES

806 DETECTING A PRESENCE AND LOCATION OF ONE OR MORE FIRST INCIDENTS OF A FIRST ATTRIBUTE

808 OUTPUTTING THE PRESENCE AND LOCATION OF THE ONE OR MORE FIRST INCIDENTS

810 DETECTING A PRESENCE AND LOCATION OF ONE OR MORE SECOND INCIDENTS OF A SECOND ATTRIBUTE

812 OUTPUTTING THE PRESENCE AND LOCATION OF THE ONE OR MORE SECOND INCIDENTS

814 COMPARING THE DETECTED LOCATIONS OF THE FIRST AND SECOND INCIDENTS

816 DETERMINING A DISEASE STATE BASED ON THE COMPARISON

818 OUTPUTTING INSTANCES WHERE THE FIRST AND SECOND ATTRIBUTES OVERLAP

FIG. 8

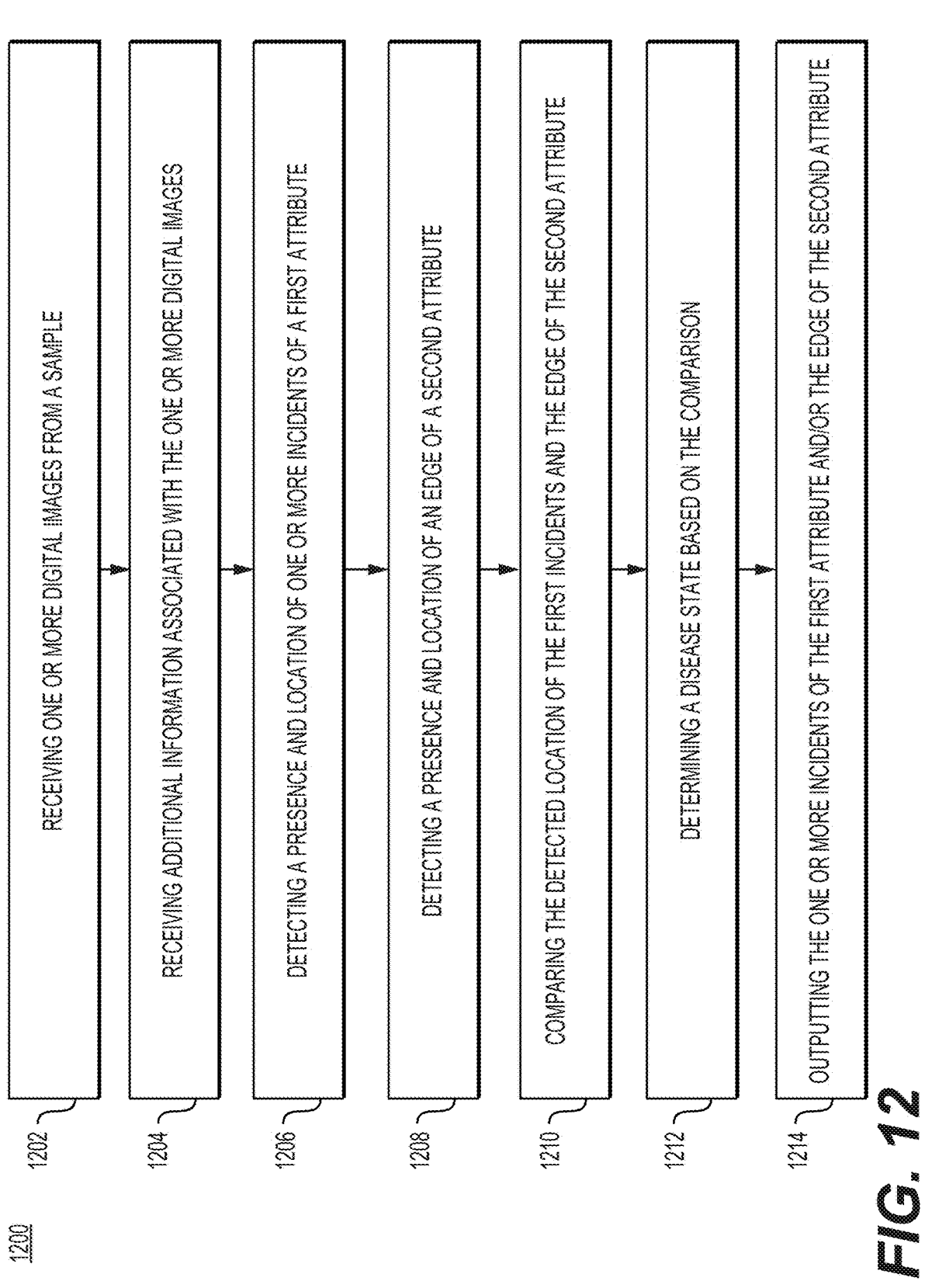

1200

1202 — RECEIVING ONE OR MORE DIGITAL IMAGES FROM A SAMPLE

1204 — RECEIVING ADDITIONAL INFORMATION ASSOCIATED WITH THE ONE OR MORE DIGITAL IMAGES

1206 — DETECTING A PRESENCE AND LOCATION OF ONE OR MORE INCIDENTS OF A FIRST ATTRIBUTE

1208 — DETECTING A PRESENCE AND LOCATION OF AN EDGE OF A SECOND ATTRIBUTE

1210 — COMPARING THE DETECTED LOCATION OF THE FIRST INCIDENTS AND THE EDGE OF THE SECOND ATTRIBUTE

1212 — DETERMINING A DISEASE STATE BASED ON THE COMPARISON

1214 — OUTPUTTING THE ONE OR MORE INCIDENTS OF THE FIRST ATTRIBUTE AND/OR THE EDGE OF THE SECOND ATTRIBUTE

FIG. 12

SYSTEMS AND METHODS FOR PROCESSING ELECTRONIC IMAGES TO VISUALIZE COMBINATIONS OF SEMANTIC PATHOLOGY FEATURES

RELATED APPLICATION(S)

This application claims priority to U.S. Provisional Application No. 63/286,604 filed Dec. 7, 2021, the entire disclosure of which is hereby incorporated herein by reference in its entirety.

FIELD OF THE DISCLOSURE

Various embodiments of the present disclosure pertain generally to image processing methods. More specifically, particular embodiments of the present disclosure relate to systems and methods to visualize combinations of semantic pathology features.

BACKGROUND

In a typical workflow, pathologists manually search slides for salient information to fill out a report of their findings. When examining a slide, a pathologist may have to identify many relevant clinical features and also spatial relationships of these features with each other.

The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

According to certain aspects of the present disclosure, systems and methods are disclosed for processing electronic images to visualize combinations of semantic pathology features.

A method for processing electronic medical images may include receiving one or more digital images of a pathology specimen, detecting a presence of one or more incidents of one or more attributes in the received digital image, detecting a spatial relationship of the one or more incidents, selecting, based on the detected spatial relationship, one or more incidents of the one or more attributes, and outputting, to a display, a visual depiction of the one or more selected incidents and the spatial relationship.

The one or more attributes may include a first attribute and a second attribute. The one or more incidents may include a first incident of the first attribute and a second incident of the second attribute. Detecting a spatial relationship of the one or more incidents may include determining a distance between the first incident and the second incident.

The method may include determining whether the first incident is co-occurring with the second incident based on the determined distance. Selecting the one or more incidents may be based on the determination of whether the first incident is co-occurring with the second incident.

The one or more attributes may include a first attribute and a second attribute. The one or more incidents may include a plurality of first incidents of the first attribute and a plurality of second incidents of the second attribute. The method may further include determining one or more incidents of co-occurrence of the first attribute and the second attribute based on the detected spatial relationship.

Selecting the one or more incidents may include selecting the incidents of co-occurrence. Outputting the visual depiction may include outputting a tissue map that indicates the incidents of co-occurrence. Outputting the visual depiction may include outputting a first selectable icon corresponding to the first attribute and a second selectable icon corresponding to the second attribute.

The one or more attributes may include a first attribute and a second attribute. The one or more incidents may include a plurality of first incidents of the first attribute and a plurality of second incidents of the second attribute. Detecting a spatial relationship may include detecting spatial relationships between the first incidents and the second incidents.

The method may further include ranking at least one of: the first incidents based on a proximity to the second incidents, the second incidents based on a proximity to the first incidents, incidents of co-occurrence, each incident of co-occurrence including at least one first incident among the plurality of first incidents that may be within a predetermined distance of a second incident among the plurality of second incidents, and/or the one or more attributes based on a predetermined policy. Selecting the one or more incidents may be based on the ranking.

The method may further include detecting that the first attribute has a higher priority than the second attribute. The method may further include detecting one or more incidents of co-occurrence of the first attribute and the second attribute. Selecting the one or more incidents may include selecting the detected one or more incidents of co-occurrence.

The method may further include detecting that there are no incidents of co-occurrence of the first attribute and the second attribute. Selecting the one or more incidents may include selecting at least one first incident.

A system may identify attributes of electronic images and display the attributes. The system may include at least one memory storing instructions and at least one processor configured to execute the instructions to perform operations. The operations may include receiving one or more digital images of a pathology specimen, detecting a presence of one or more incidents of one or more attributes in the received digital image, detecting a spatial relationship of the one or more incidents, selecting, based on the detected spatial relationship, one or more incidents of the one or more attributes, and outputting, to a display, a visual depiction of the one or more selected incidents and the spatial relationship.

The one or more attributes may include a first attribute and a second attribute. The one or more incidents may include a first incident of the first attribute and a second incident of the second attribute. Detecting a spatial relationship of the one or more incidents may include determining a distance between the first incident and the second incident.

The operations may include determining whether the first incident is co-occurring with the second incident based on the determined distance. Selecting the one or more incidents may be based on the determination of whether the first incident is co-occurring with the second incident.

The one or more attributes may include a first attribute and a second attribute. The one or more incidents may include a plurality of first incidents of the first attribute and a plurality of second incidents of the second attribute. The operations may include determining one or more incidents of co-occurrence of the first attribute and the second attribute based on the detected spatial relationship.

Selecting the one or more incidents may include selecting the incidents of co-occurrence. Outputting the visual depiction may include outputting a tissue map that indicates the incidents of co-occurrence. Outputting the visual depiction may include outputting a first selectable icon corresponding to the first attribute and a second selectable icon corresponding to the second attribute.

A non-transitory computer-readable medium storing instructions that, when executed by a processor, perform a method for identifying attributes of electronic images and displaying the attributes. The method may include receiving one or more digital images of a pathology specimen, detecting a presence of one or more incidents of one or more attributes in the received digital image, detecting a spatial relationship of the one or more incidents, selecting, based on the detected spatial relationship, one or more incidents of the one or more attributes, and outputting, to a display, a visual depiction of the one or more selected incidents and the spatial relationship.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIG. 2 illustrates a flowchart illustrating an exemplary method for detecting and outputting incidents of attributes, according to an example embodiment.

FIG. 3 illustrates a flowchart illustrating an exemplary method for visualizing detected incidents of attributes, according to an example embodiment.

FIG. 4 is a flowchart illustrating an exemplary method for detecting incidents of co-occurrence of attributes, according to an example embodiment.

FIG. 6 is a flowchart illustrating an exemplary method for detecting and outputting incidents of a first attribute and a second attribute, according to an example embodiment.

FIG. 7 is a flowchart illustrating an exemplary method for detecting and outputting incidents of a predetermined muscle and an invasion, according to an example embodiment.

FIG. 8 is a flowchart illustrating an exemplary method for outputting incidents of a first attribute and a second attribute, according to an example embodiment.

FIG. 12 is a flowchart illustrating an exemplary method for detecting and outputting incidents of a first attribute and an edge of a second attribute, according to an example embodiment.

DESCRIPTION OF THE EMBODIMENTS

Figure 1A:
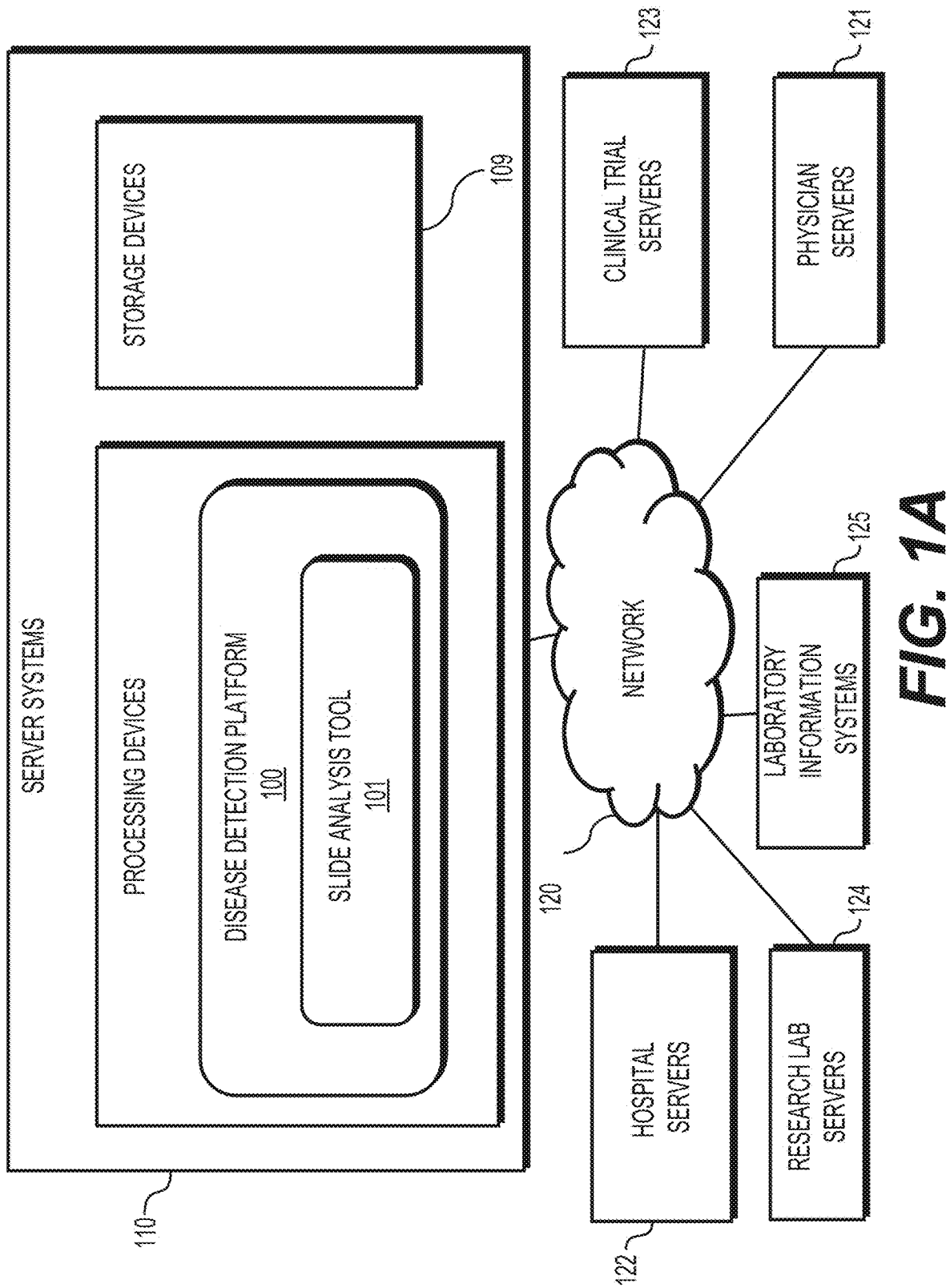
FIG. 1A illustrates an exemplary block diagram of a system and network to identify salient attributes of digital or electronic slide images and to follow a policy or strategy of smoothly displaying (via zooming, panning, etc.) the identified salient attributes, according to an exemplary embodiment of the present disclosure.

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items.

Technical aspects disclosed herein may provide policies for semantic logic that enable a more complex interaction between a user or pathologist and artificial intelligence (AI) findings. Technical aspects disclosed herein may enhance an AI-assisted process of clinical sign out, or a process of transferring information from one user to another. Technical aspects disclosed herein may significantly increase a complexity of interaction with outputs of an AI system.

Numerous tasks in anatomic pathology may involve an evaluation of a spatial intersection of two attributes. Pathologists may use a spatial relationship of many identified relevant clinical features to assist in diagnosis and/or treatment. Perineural invasion assessment across cancer types may involve visualization of cancerous cells around and within nerves. Various cancers may be staged and evaluated based on their presence within other microanatomical structures such as muscular layers. For example, colon cancer staging may be evaluated based on presence within various muscle layers.

As another example, when reviewing a bladder tissue sample for cancer, a pathologist may identify a presence of the cancer and a presence of muscularis propria, and the pathologist may assess a spatial proximity of the cancer and muscularis propria to determine if there has been invasion. In this example, the pathologist may desire to see a region where the muscularis propria is closest to (and/or overlapping with) the cancer versus any randomly selected area of muscularis propria or any randomly selected area of cancer. The muscularis propria closest to the cancer may be a most relevant location or salient region to observe if both muscularis propria and cancer are present. If there was no invasion, then a next most relevant feature may be cancer. If cancer was not present, then a next most relevant feature may be muscularis propria alone. This ranking of priority for reviewing of findings on a slide may be applied to contexts other than bladder cancer, including breast, prostate, and colon cancer. For example, calcifications that overlap with ductal carcinoma in situ (DCIS) in a breast biopsy may indicate an invasion.

In an AI-powered workflow, an AI or machine learning (ML) system may determine a presence or absence of many attributes to be reported. However, just showing a presence or absence might not assist pathologists in identifying spatial relationships among these attributes. Reporting identified or present attributes and their relation to other identified or present attributes may provide more information.

An AI system may output distinct clinical findings for digital whole slide images (WSIs) for a tissue type, e.g., a bladder system. The AI system may spatially localize a variety of distinct attributes such as finding a location of cancer and finding a location of muscularis propria.

The AI system may use policies or rules to prioritize how these spatial locations of attributes should be reviewed by pathologists. For example, the AI system may incorporate policies regarding how to prioritize identified attributes based on relationships between more than one attribute. These policies may be customized by a user, by a regulatory agency, or come from some other source. Multiple policies for a tissue type may be incorporated, and a user may select among these multiple policies to traverse or navigate one or more slides from a patient.

Figure 1B:
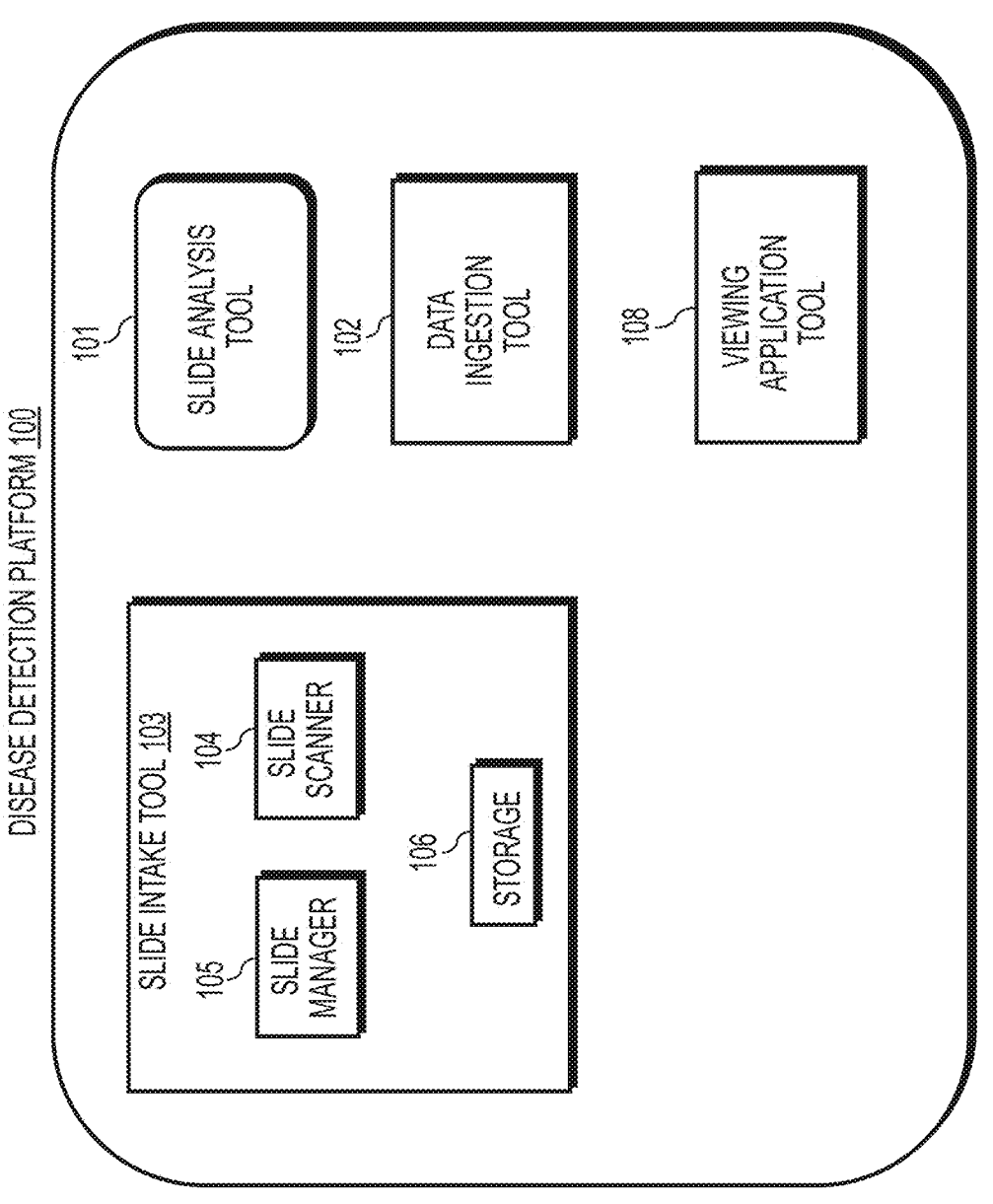
FIG. 1B illustrates an exemplary block diagram of a disease detection platform, according to an exemplary embodiment of the present disclosure.
Figure 1C:
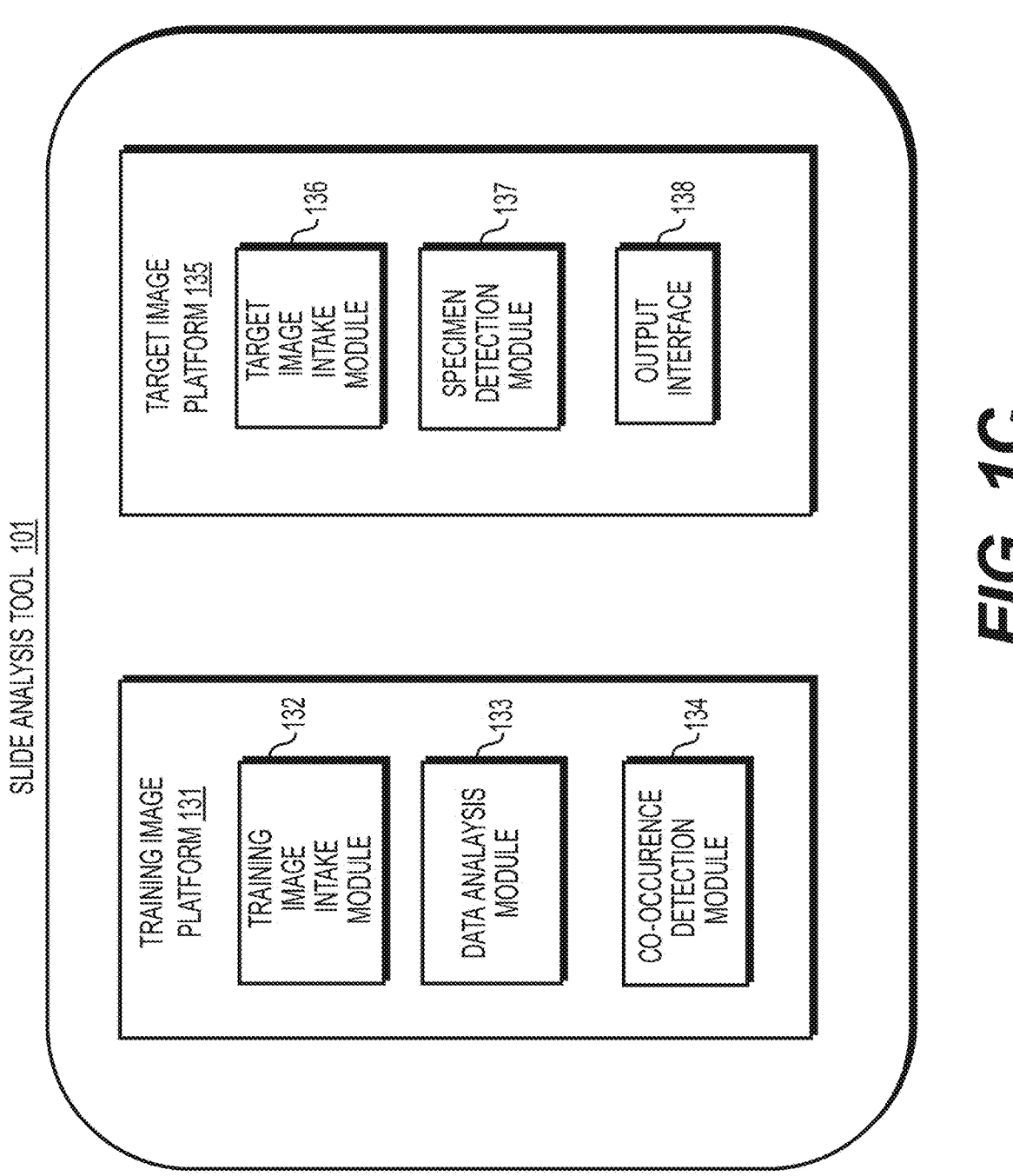
FIG. 1C illustrates an exemplary block diagram of a slide analysis tool, according to an exemplary embodiment of the present disclosure.

FIGS. 1A through 1C show a system and network to identify salient attributes of digital slide images and their spatial relationships, according to an exemplary embodiment of the present disclosure.

Specifically, FIG. 1A illustrates an electronic network 120 that may be connected to servers at hospitals, laboratories, and/or doctor's offices, etc. For example, physician servers 121, hospital servers 122, clinical trial servers 123, research lab servers 124, and/or laboratory information systems 125, etc., may each be connected to an electronic network 120, such as the Internet, through one or more computers, servers and/or handheld mobile devices. According to an exemplary embodiment of the present application, the electronic network 120 may also be connected to server systems 110, which may include processing devices that are configured to implement a disease detection platform 100, which includes a slide analysis tool 101 for determining specimen property or image property information pertaining to digital pathology image(s), and using machine learning to determine whether a disease or infectious agent is present, according to an exemplary embodiment of the present disclosure. The slide analysis tool 101 may allow for rapid evaluation of 'adequacy' in liquid-based tumor preparations, facilitate the diagnosis of liquid based tumor preparations (cytology, hematology/hematopathology), and predict molecular findings most likely to be found in various tumors detected by liquid-based preparations.

The physician servers 121, hospital servers 122, clinical trial servers 123, research lab servers 124 and/or laboratory information systems 125 may create or otherwise obtain images of one or more patients' cytology specimen(s), histopathology specimen(s), slide(s) of the cytology specimen(s), digitized images of the slide(s) of the histopathology specimen(s), or any combination thereof. The physician servers 121, hospital servers 122, clinical trial servers 123, research lab servers 124 and/or laboratory information systems 125 may also obtain any combination of patient-specific information, such as age, medical history, cancer treatment history, family history, past biopsy or cytology information, etc. The physician servers 121, hospital servers 122, clinical trial servers 123, research lab servers 124 and/or laboratory information systems 125 may transmit digitized slide images and/or patient-specific information to server systems 110 over the electronic network 120. Server system(s) 110 may include one or more storage devices 109 for storing images and data received from at least one of the physician servers 121, hospital servers 122, clinical trial servers 123, research lab servers 124, and/or laboratory information systems 125. Server systems 110 may also include processing devices for processing images and data stored in the storage devices 109. Server systems 110 may further include one or more machine learning tool(s) or capabilities. For example, the processing devices may include a machine learning tool for a disease detection platform 100, according to one embodiment. Alternatively or in addition, the present disclosure (or portions of the system and methods of the present disclosure) may be performed on a local processing device (e.g., a laptop).

The physician servers 121, hospital servers 122, clinical trial servers 123, research lab servers 124 and/or laboratory information systems 125 refer to systems used by pathologists for reviewing the images of the slides. In hospital settings, tissue type information may be stored in a laboratory information system 125.

FIG. 1B illustrates an exemplary block diagram of a disease detection platform 100 for determining specimen property or image property information pertaining to digital pathology image(s), using machine learning. The disease detection platform 100 may include a slide analysis tool 101, a data ingestion tool 102, a slide intake tool 103, a slide scanner 104, a slide manager 105, a storage 106, a laboratory information system 107, and a viewing application tool 108.

The slide analysis tool 101, as described below, refers to a process and system for determining data variable property or health variable property information pertaining to digital pathology image(s). Machine learning may be used to classify an image, according to an exemplary embodiment. The slide analysis tool 101 may also predict future relationships, as described in the embodiments below.

The data ingestion tool 102 may facilitate a transfer of the digital pathology images to the various tools, modules, components, and devices that are used for classifying and processing the digital pathology images, according to an exemplary embodiment.

The slide intake tool 103 may scan pathology images and convert them into a digital form, according to an exemplary embodiment. The slides may be scanned with slide scanner 104, and the slide manager 105 may process the images on the slides into digitized pathology images and store the digitized images in storage 106.

The viewing application tool 108 may provide a user with a specimen property or image property information pertaining to digital pathology image(s), according to an exemplary embodiment. The information may be provided through various output interfaces (e.g., a screen, a monitor, a storage device and/or a web browser, etc.).

The slide analysis tool 101, and one or more of its components, may transmit and/or receive digitized slide images and/or patient information to server systems 110, physician servers 121, hospital servers 122, clinical trial servers 123, research lab servers 124, and/or laboratory information systems 125 over a network 120. Further, server systems 110 may include storage devices for storing images and data received from at least one of the slide analysis tool 101, the data ingestion tool 102, the slide intake tool 103, the slide scanner 104, the slide manager 105, and viewing application tool 108. Server systems 110 may also include processing devices for processing images and data stored in the storage devices. Server systems 110 may further include one or more machine learning tool(s) or capabilities, e.g., due to the processing devices. Alternatively, or in addition, the present disclosure (or portions of the system and methods of the present disclosure) may be performed on a local processing device (e.g., a laptop).

Any of the above devices, tools, and modules may be located on a device that may be connected to an electronic network such as the Internet or a cloud service provider, through one or more computers, servers and/or handheld mobile devices.

FIG. 1C illustrates an exemplary block diagram of a slide analysis tool 101, according to an exemplary embodiment of the present disclosure. The slide analysis tool 101 may include a training image platform 131 and/or a target image platform 135.

According to one embodiment, the training image platform 131 may include a training image intake module 132, a data analysis module 133, and a co-occurrence detection module 134.

The training data platform 131, according to one embodiment, may create or receive training images that are used to train a machine learning model to effectively analyze and classify digital pathology images. For example, the training images may be received from any one or any combination of the server systems 110, physician servers 121, hospital servers 122, clinical trial servers 123, research lab servers 124, and/or laboratory information systems 125. Images used for training may come from real sources (e.g., humans, animals, etc.) or may come from synthetic sources (e.g., graphics rendering engines, 3D models, etc.). Examples of digital pathology images may include (a) digitized slides stained with a variety of stains, such as (but not limited to) hematoxylin and eosin (H&E), Hematoxylin alone, immunohistochemistry (IHC), molecular pathology, etc.; and/or (b) digitized tissue samples from a 3D imaging device, such as microCT.

The training image intake module 132 may create or receive a dataset comprising one or more training datasets corresponding to one or more health variables and/or one or more data variables. For example, the training datasets may be received from any one or any combination of the server systems 110, physician servers 121, hospital servers 122, clinical trial servers 123, research lab servers 124, and/or laboratory information systems 125. This dataset may be kept on a digital storage device. The data analysis module 133 may identify whether an area belongs to a region of interest or salient region, or to a background of a digitized image. The co-occurrence detection module 134 may analyze digitized images to detect or identify salient and/or relevant attributes, their spatial locations, whether one or more attributes are co-occurring and/or overlap, and/or whether a region and/or attribute in the sample needs further analysis. The identification of a salient attribute and/or co-occurrence may trigger an alert to a user.

According to one embodiment, the target image platform 135 may include a target image intake module 136, a specimen detection module 137, and an output interface 138. The target image platform 135 may receive a target image and apply the machine learning model to the received target image to determine a characteristic of a target data set. For example, the target data may be received from any one or any combination of the server systems 110, physician servers 121, hospital servers 122, clinical trial servers 123, research lab servers 124, and/or laboratory information systems 125. The target image intake module 136 may receive a target dataset corresponding to a target health variable or a data variable. Specimen detection module 137 may apply the machine learning model to the target dataset to determine a characteristic of the target health variable or a data variable. For example, the specimen detection module 137 may detect a trend of the target relationship. The specimen detection module 137 may also apply the machine learning model to the target dataset to determine a quality score for the target dataset. Further, the specimen detection module 137 may apply the machine learning model to the target images to determine whether a target element is present in a determined relationship.

The output interface 138 may be used to output information about the target data and the determined relationship (e.g., to a screen, monitor, storage device, web browser, etc.). The output interface 138 may display identified attributes of analyzed slides and their spatial relationship according to a policy or strategy.

An AI system (e.g., a system using disease detection platform 100) may process a given tissue type based on a form of digital or electronic medical images (e.g., whole slide images or WSIs) and output (e.g., on output interface 138) one or more attributes about the tissue type. The AI system may further output locations of each of these attributes. Locations could be specified and/or output as positional coordinates, polygons, a pixel mask (e.g., tissue map), or other form of data that indicates a presence of each attribute and its spatial location(s).

Here, the AI system may refer to one or more AI, ML, and/or deep learning systems, platforms, or processes. For example, one AI platform or process may output presence/absence and location data for one type of attribute, another AI platform or process may output presence/absence and location type for another type of attribute, etc. Aspects disclosed herein are not limited to an arrangement of the AI system.

For a given tissue type, locations and/or spatial characteristics of the detected attributes may be compared. If the detected locations are similar (e.g., within a same predefined distance, radius, or area), the attributes may be co-occurring. For example, for a given tissue type, a distance threshold or other position value (or alternatively or in addition thereto, an area value or other spatial value) for each attribute may be defined or predetermined. The distance threshold may be used to determine whether multiple attributes are co-occurring together. For example, the distance threshold may be a predetermined or prescribed distance (e.g., in microns) between the detected muscularis propria and cancer. An output or sensed distance (or difference in sensed distances) which is less than or equal to the distance threshold may indicate invasion and/or a co-occurrence relationship.

For a given tissue type, a policy may be defined or prescribed to determine a priority order or list in which information should be processed. This priority order or list may rank the following for a given tissue type: (1) each co-occurrence relationship's priority for review by a user, and (2) each individual attribute's and/or incident's priority for review by a user.

The determined priority order or list, along with distance measurements and/or distance thresholds, may be saved to electronic storage, e.g., cloud storage, hard disk, RAM, etc.

Referring to FIGS. 2-3, aspects disclosed herein may provide a method 200 of analyzing salient or relevant attributes on one or more digital images (e.g., whole slide image or WSI) and a method 300 of visualizing those attributes and/or other semantic features. FIGS. 4-17 may provide examples of analyzing exemplary attributes and/or exemplary visualizations of the attributes.

Referring to FIG. 2, a method 200 of may include a step 202 of receiving one or more digital images (e.g., whole slide images or WSIs) for a specimen and/or patient. Step 202 may also include receiving additional information associated with the specimen, patient, or received image, such as tissue type, patient information, etc.

The method 200 may include a step 202 of detecting a presence of one or more incidents of one or more attributes in the received digital image. The attributes may be relevant or salient attributes, such as a salient region (e.g., a region that may be indicative of a disease such as cancer, tumor tissue, etc.), a region or feature of interest for further analysis, a predetermined tissue or muscle (e.g., muscularis propria), etc. Salient regions may be detected based on feature size, calcification presence and/or level, color, stain type or color, tissue texture, tissue type, biomarker type, genetic signature, protein type, blood markers, tissue location, inflammation level, and/or combination thereof. Salient region detection may include methods discussed in U.S. application Ser. No. 17/313,617, which is incorporated by reference herein in its entirety. Step 204 may include applying a machine learning system and/or artificial intelligence model, such as the slide analysis tool 101 and/or the co-occurrence detection module 134 described with reference to FIG. 1C.

Here, the attribute may be a type of attribute (e.g., muscularis propria, calcification, ductal carcinoma in situ (DCIS), etc.), while an incident may be a detected spatial location or individual presence of the attribute. For example, a WSI may include a plurality of incidents or regions having a same attribute.

The method 200 may include a step 206 of detecting a spatial relationship among the one or more incidents of the one or more attributes. For example, detecting the spatial relationship may include determining a location within the digital image of each incident. As another example, detecting the spatial relationship may include detecting distances between incidents of a plurality of incidents. In yet another example, where the one or more attributes includes multiple attributes (e.g., multiple types such as a muscle and abnormal cells), detecting the spatial relationship may include determining relative distances between instances of one type and instance of another type. Step 206 may include applying a machine learning system and/or artificial intelligence model, such as the slide analysis tool 101 and/or the co-occurrence detection module 134 described with reference to FIG. 1C.

The method 200 may include a step 208 of selecting, based on the detected spatial relationship, one or more incidents of the one or more attributes, and a step 210 of outputting, to a display, a visual depiction of the one or more selected incidents and the spatial relationship. For example, step 208 may include selecting incidents belonging to a predetermined type of attribute and/or a determined most relevant type of attribute, and step 210 may include outputting a tissue map of the selected incidents. As another example, step 208 may include selecting incidents according to a predetermined policy that determines a priority level of each incident and/or each type of attribute. In yet another example, step 208 may include selecting incidents based on their proximities and/or their type. For example, step 206 may include determining distances between incidents in a pair or group of incidents, each group including an incident of a first type of attribute and an incident of a second type of attribute, and step 208 may include selecting pairs where the distance between the incidents is less than a predetermined threshold. Step 208 may include selecting co-occurrences of two types of attributes, as described in more detail with reference to FIG. 4. Step 208 may include ranking detected incidents and/or attribute types based on their spatial relationships (e.g., proximities to incidents of another type) and/or predetermined priority levels or other scores, and selecting the incidents above a predetermined number in the ranking (e.g., the first five incidents and/or incidents of co-occurrence in the ranking, or all incidents of the first two attributes in the ranking, etc.)

Referring to FIG. 3, a method 300 of visualizing attributes may include a step 302 of detecting one or more incidents of one or more attributes. Detecting the one or more incidents may include detecting an attribute type for each incident. Step 302 may also include detecting a spatial relationship of the one or more incidents. Step 302 may include receiving additional information such as a tissue type, patient information, etc., associated with the one or more digital images. The method 300 may include a step 304 of generating a tissue map, such as exemplified in FIGS. 9-11. The tissue map may visually display the detected incidents of attributes and their detected spatial relationships. The tissue map may be used to relevant relationships among the detected attributes as one or more extrapolated new attribute masks, polygons, etc. for combinations of binary attributes.

The detected spatial relationships and/or attribute types may be indicative of an incidence of co-occurrence between a first attribute and a second attribute, the first attribute being a different attribute than the second attribute (e.g., DCIS versus muscle). In addition, each detected incident, each attribute, and/or each incident of co-occurrence may have a priority level according to a predetermined policy or according to detected parameters.

The method 300 may include a step 306 of displaying one or more incidents of co-occurrence of a first attribute and a second attribute according to a priority level of each incident of co-occurrence. For example, incidents of co-occurrence having a certain priority level or greater (e.g., based on attribute types of the incidents and/or based on a proximity between the incidents) may be flagged, boxed, highlighted, colored, enlarged, annotated, etc. on the generated tissue map.

The method 300 may include a step 308 of displaying one or more selectable icons, each icon corresponding to the one or more attributes (e.g., DCIS or muscle). When a user selects an icon corresponding to an attribute (e.g., DCIS), the incidents of DCIS and/or incidents of DCIS having a certain priority level (e.g., due to proximity to another attribute and/or based on a spatial location) may be displayed and/or indicated, such as by being flagged, boxes, highlighted, colored, enlarged, annotated, etc. on the generated tissue map. Where certain attributes are not detected (e.g., calcification or other attributes), a selectable icon may not appear and/or may be grayed out.

The method 300 may include a step 310 of displaying the detected one or more incidents in an order based on a priority level, ranking, or other parameter associated with each incident and/or each attribute. For example, step 310 may include automatically panning to, jumping to, and/or indicating (e.g., through flags, boxes, highlighting, coloring, annotating, zooming in, enlarging, etc.) through the detected incidents based on the priority level. Step 310 may also include displaying a panel with information relating to each incident, such as attribute type, a classification, priority level, diagnosis, severity, patient information, etc. FIGS. 5A-5D provide further details on displaying detected incidents and/or attributes according to priority level, scores, etc.

Referring to FIG. 4, aspects disclosed herein may include determining incidents of co-occurrence or overlap between two or more attributes. A method 400 of visualizing combinations of semantic features and/or using an AI system may include a step 402 of receiving one or more digital images (e.g., whole slide images or WSIs) for a patient and/or a portion of a specimen into electronic or digital storage. The method 400 may include a step 404 of receiving additional information, such as a tissue type, patient information, etc., associated with the one or more digital images into electronic storage. The additional information may be received with the received digital image(s).

The method 400 may include a step 406 of identifying or detecting a presence (or absence) of one or more incidents of one or more attributes based on the received one or more digital images. The attributes may be relevant or salient attributes, such as a salient region (e.g., a region that may be indicative of a disease such as cancer, tumor tissue, etc.), a region or feature of interest for further analysis, a predetermined tissue or muscle (e.g., muscularis propria), etc. Salient regions may be detected based on feature size, calcification presence and/or level, color, stain type or color, tissue texture, tissue type, biomarker type, genetic signature, protein type, blood markers, tissue location, inflammation level, and/or combination thereof. Step 406 may include using an AI system for that tissue type, co-registered IHCs and/or immunofluorescent images, human or manual annotations received as additional information in step 404, etc. Determined spatial locations may have zero or more non-mutually exclusive attributes within the slide. Step 406 may include identifying or determining a type of attribute. Step 406 may include identifying all relevant attributes on each slide with their spatial locations.

Step 406 may include running or applying an AI system (e.g., including a machine learning model) on each received digital image for a patient to identify the presence (or absence) of the one or more attributes. Running the AI system may include running multiple AI systems, platforms, or processes respectively corresponding to the one or more attributes, but aspects disclosed herein are not limited to an organization of the AI system.

The method 400 may include a step 408 of detecting or determining a spatial location of each of the detected incidents. Step 408 may be performed using an AI system (e.g., the AI system used in step 406) or manually. Step 408 may include determining a spatial location on the one or more received images. Alternatively or in addition thereto, where multiple attributes and/or multiple types of attributes are detected in step 406, step 408 may include detecting relative spatial locations and/or distances between or among the detected attributes and/or detected types of attributes (e.g., a first type and a second type).

Step 408 may be performed using an AI system configured to a type of tissue associated with the one or more digital images, immunostaining, co-registered immunohistochemistry (IHC), immunofluorescent images, and/or human or manual annotations. IHC stains may provide biological information related to attributes that may be predicted by the AI system. Pathologists may benefit from an ability to visualize an AI-predicted or AI-detected attribute derived from hematoxylin and eosin (H&E) stained tissue on the IHC stained tissue, allowing the pathologist to integrate AI data with biological immunohistochemical data.

Spatial locations may have zero or more non-mutually exclusive attributes within a digital image. Each attribute may be represented as a binary or probability attribute mask over the tissue, a polygon, etc. Step 408 may include outputting, to a display and/or electronic storage, a tissue map such as a tissue maps 902, 1002, and/or 1102 shown in FIGS. 9-11 to indicate the detected attributes and/or attribute types and spatial locations.

Where multiple attributes are detected in step 406, the method 400 may include a step 410 of determining, based on the determined attributes and spatial locations, a co-occurrence of the attributes and/or related clinical findings. Step 410 may include using predetermined distance thresholds or other predetermined spatial values to determine which attributes are co-occurring with each other. Step 410 may include determining other relationships (e.g., non-overlapping) among the detected attributes. Here, attributes may mean an attribute type (e.g., DCIS or muscle), whereas an incident may mean an incident of an individual attribute. In some examples, step 410 may include determining incidents of co-occurrence and/or a density of one attribute, such as DCIS, where, for example, multiple incidents of DCIS are within a same area or region.

For example, the method 400 may include, in step 408, determining or calculating distances between the multiple attributes and, in step 410, determining whether these calculated distances are at or below a predetermined distance threshold. Alternatively or in addition thereto, the steps 408 and 410 may include using a spatial-relationship and co-occurrence module (e.g., an AI system or machine learning model) to identify relationships among attributes.

Figure 9:
FIG. 9 shows an exemplary display indicating a first attribute, according to an example embodiment.
Figure 10:
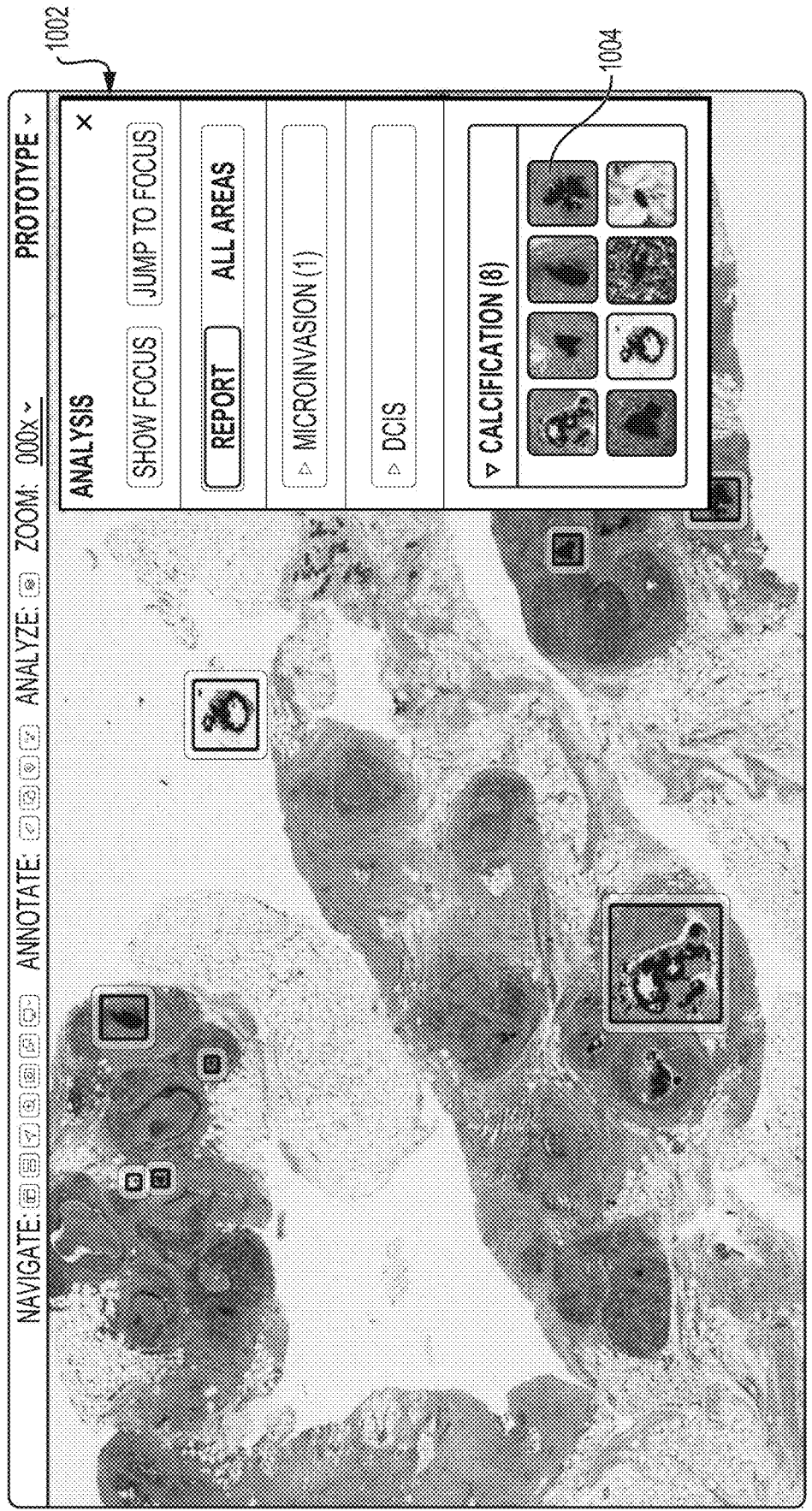
FIG. 10 shows an exemplary display indicating a second attribute, according to an example embodiment.
Figure 11:
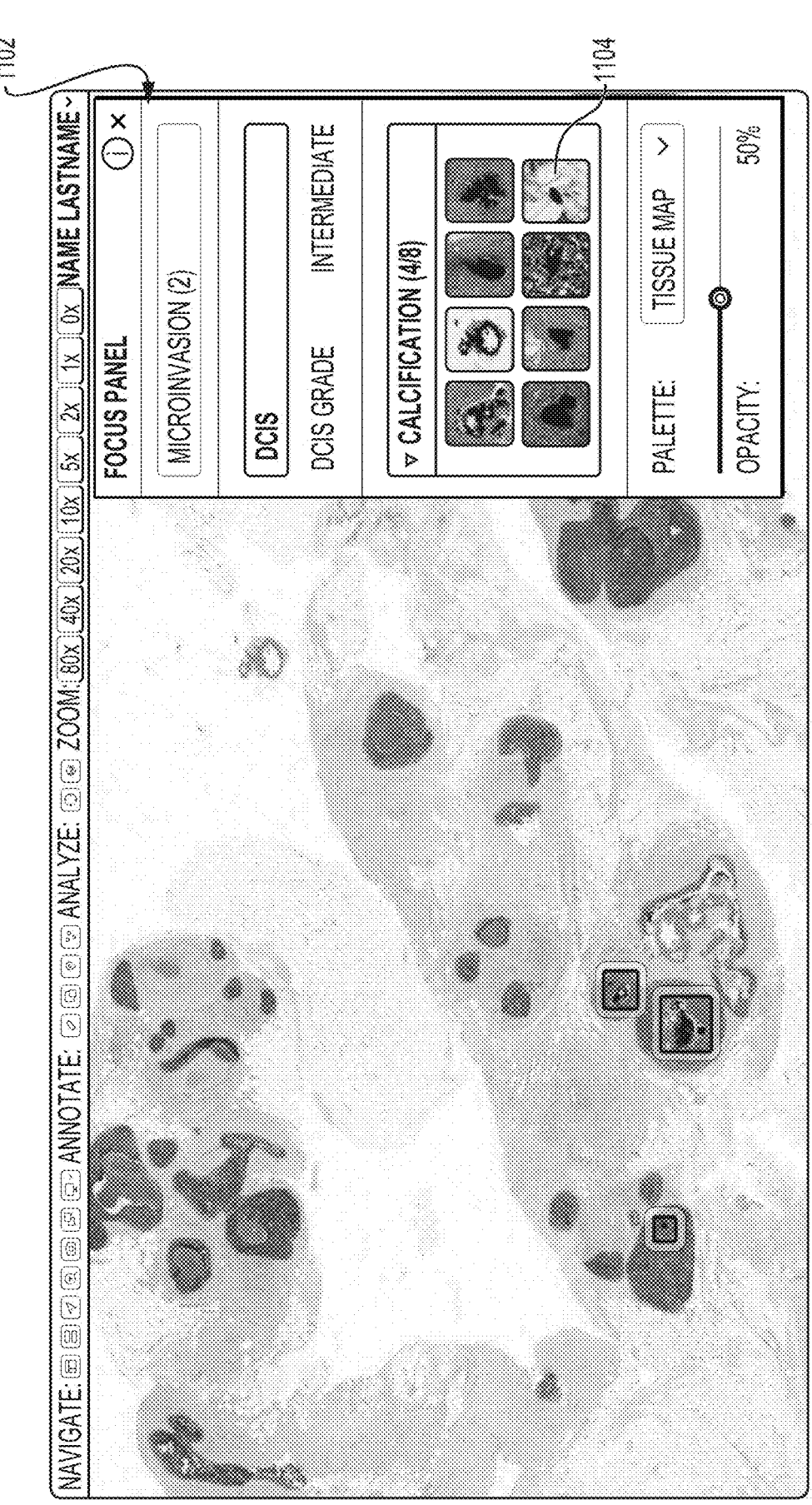
FIG. 11 shows an exemplary display indicating incidents of co-occurrence of a first attribute and a second attribute, according to an example embodiment.

The method 400 may include a step 412 of outputting determined relationships to a display and/or electronic storage. The determined relationships may include determined spatial locations (determined in step 408) and/or determined co-occurrences (e.g., as in step 410). This step 412 may include outputting relevant relationships among the detected attributes as one or more extrapolated new attribute masks, polygons, etc. for combinations of binary attributes. These outputs may be stored to electronic storage and/or displayed on a user interface. For example, the method 400 may include a step 412 of outputting the determinations to a display and/or electronic storage. Step 412 may include generating and/or displaying a tissue map from H&E stains and/or displaying an overlap on an IHC stain to indicate the determined attributes, their spatial locations, and/or their co-occurrences. FIGS. 9, 10, and 11 may show exemplary outputs in the form of tissue maps 902, 1002, and/or 1102.

Step 412 may include providing or presenting a user of the display with different buttons, selectable icons, thumbnails images, and/or screens that highlight incidents, incidents of individual attributes, and/or co-occurring attributes. Step 412 may include disabling or otherwise indicating buttons or selectable icons in which no findings of a corresponding attribute are present. For example, if no cancer is identified or detected, then a button, selectable icon, or thumbnail corresponding to cancer may be greyed out. The provided user interface in step 412 may be based on one or more determined scores, priority levels, policies, etc. associated with the detected attributes, as explained in more detail with reference to FIGS. 5A-5D. For example, step 412 may include providing a user interface that allows a user to display one or more findings (e.g., individual attributes or incidents of an attribute, a certain attribute type, instances of co-occurrence, and/or instance of non-overlap) in a variety of ways and/or that displays the one or more findings based on a priority level or policy. The user interface may allow a user to see all findings in their entireties, to see only an overlap of findings (e.g., incidents of co-occurrence), to see non-overlapping findings or incidents only, or to see only areas where the AI system may be less confident or more uncertain or in between two classifications of finding or values (e.g., two different grades for DCIS).

Step 412 may include performing one or more detections or determinations to display the incidents and/or attributes. Referring to FIG. 4, step 412 may be implemented as a method 500 for determining a display of detected attributes.

Priority Review System

Determining a display or output may be performed without performing detection. For example, Referring to FIG. 5A, the method 500 may include a step 502 of receiving spatial locations and/or co-occurrences of attributes (e.g., that have been detected by another module and/or system). For example, step 502 may include receiving detected spatial locations and/or co-occurrences of attributes detected on one or more received digital images, as determined in steps 408 and 410 described with reference to FIG. 4. Alternatively or in addition thereto, step 502 may include detecting or determining spatial locations and/or co-occurrences of attributes, such as by using an AI module or machine learning system.

The method 500 may include a step 504 of receiving additional information associated with the attributes. For example, step 504 may include receiving the additional information (e.g., tissue type) received in step 404 described with reference to FIG. 4. As another example, steps 502 and 504 may be replaced with steps 402 and 404 described with reference to FIG. 4.

The method 500 may include a step 506 of applying one or more policies or strategies to determine one or more displays. For example, step 506 may include applying one or more policies to determine which attributes to display, which areas of a digital image to display, which attributes to highlight, what additional information to display (e.g., tissue type or attribute type), zoom-in on, jump-to, pan to, etc. The policy or strategy may be predetermined and/or based on user input. The method 500 may include a step 508 outputting the determined display.

For example, in step 506, applying the policy may result in determining that the display should show all attributes, occurrence determinations, and/or other findings in their entirety (e.g., simultaneously on one screen), and step 508 may include displaying all attributes, co-occurrence determinations, and other findings (e.g., including an entire image issued, the detected attributes, their spatial locations, and their co-occurrences). As another example, step 506 may include determining that the display should show only an overlap of multiple findings or co-occurrences (or alternatively, only non-overlapping areas of findings), and step 508 may include displaying only the overlap of multiple findings of co-occurrences (or alternatively, only non-overlapping areas of findings).

Figure 5A:
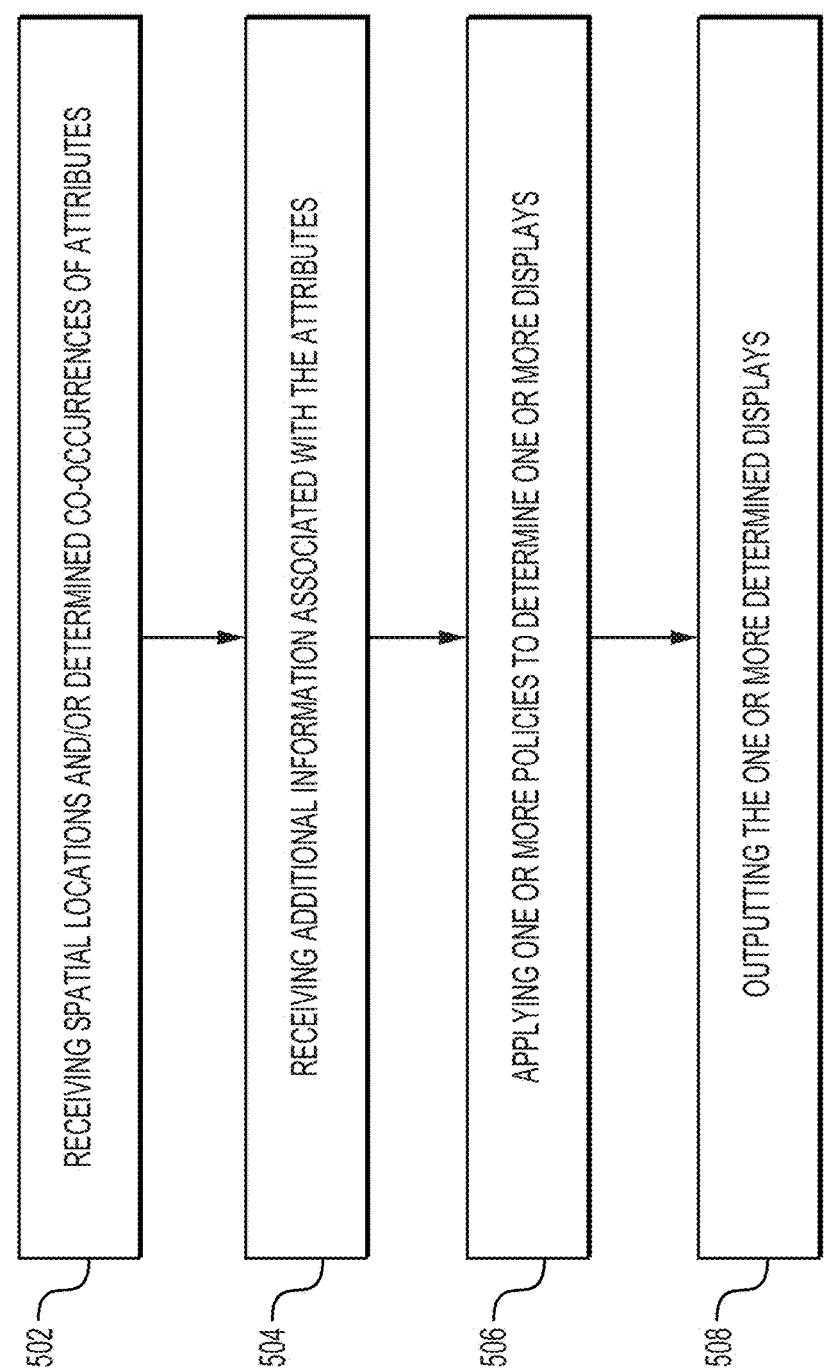
FIG. 5A is a flowchart illustrating an exemplary method for selecting and/or outputting incidents of attributes based on one or more policies, according to an example embodiment.
Figure 5B:
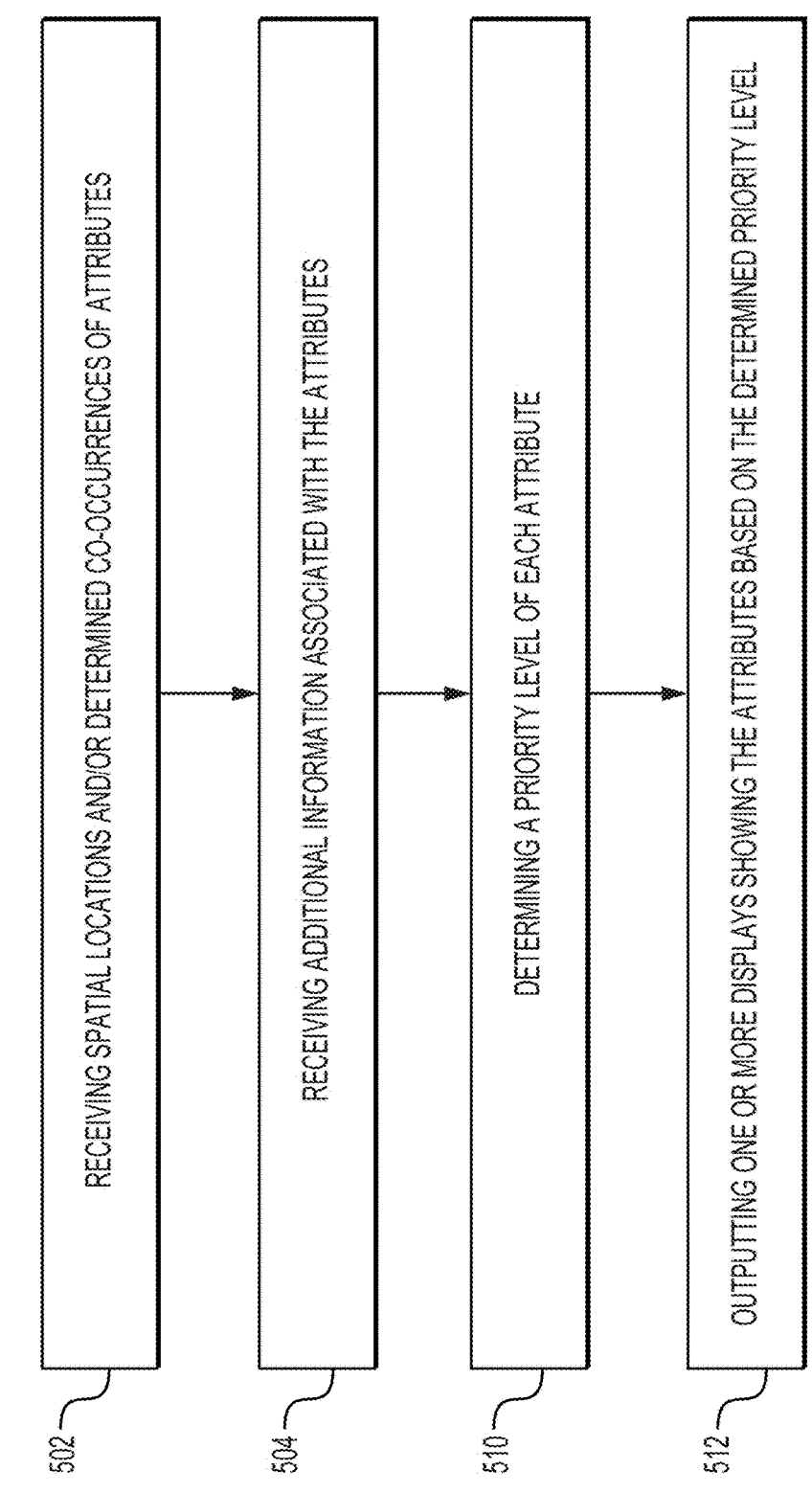
FIG. 5B is a flowchart illustrating an exemplary method for selecting and/or outputting incidents of attributes based on a priority level, according to an example embodiment.

Referring to FIG. 5B, in some examples, the method 500 may include a step 510 of determining a priority level or value for each attribute, attribute type, and/or each incidence of co-occurrence or overlap of attributes (e.g., by applying a policy, AI system, or machine learning model) and a step 512 of outputting one or more displays of the attributes based on the predetermined priority level. In some examples, the policy may include a predetermined priority of attributes. Step 506 of FIG. 5A may include step 510, and step 508 of FIG. 5A may include step 512.

Step 512 may include providing a user with different buttons or selectable icons that indicate or highlight individual incidents, individual attributes, and/or co-occurring attributes. Step 512 may include disabling buttons or selectable icons (e.g., greying out buttons) in which no findings are present (e.g., no detected cancer). Step 512 may include providing or presenting a "jump-to" button or input option that allows a user to jump to displays of certain findings of attributes based on (e.g., in ascending or descending order of) the determined priority levels. Alternatively or in addition thereto, step 512 may include providing an automated panning button that allows a user to jump from or between displays of attributes or findings based on (e.g., in ascending or descending order of) the determined priority levels and/or policy.

Figure 5C:
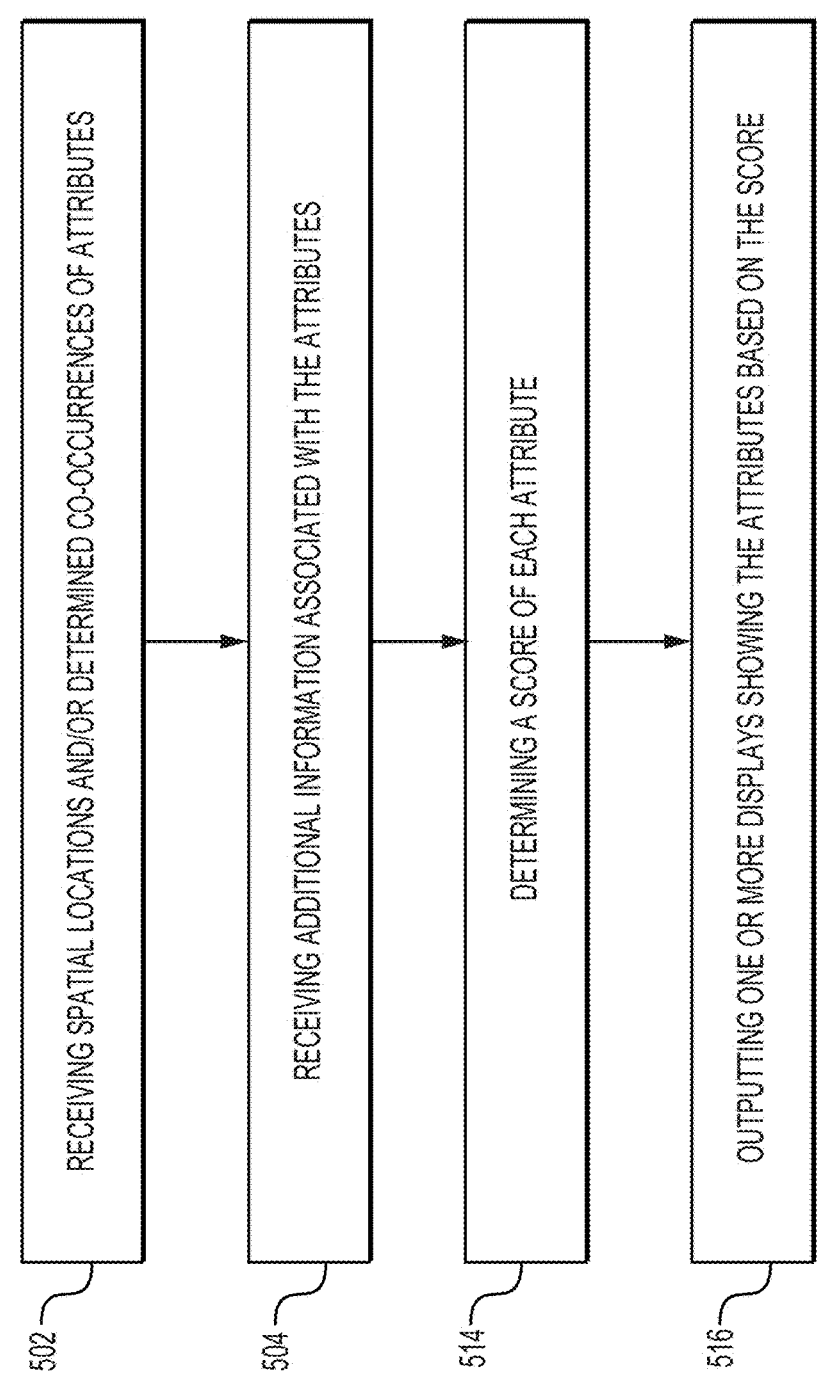
FIG. 5C is a flowchart illustrating an exemplary method for selecting and/or outputting incidents of attributes based on one or more scores, according to an example embodiment.

Referring to FIG. 5C, in some examples, the method 500 may include a step 514 of determining a score or value for each attribute, determined co-occurrence, or other finding (e.g., by applying a policy, AI system, or machine learning model), and a step 516 of outputting a display of the attributes according to the determined score. For example, step 514 may include determining a certainty or confidence value in a finding of a co-occurrence or an attribute, an overlapping of findings, a classification of a finding, a determination of an attribute type, etc., and step 516 may include displaying and/or indicating regions where there is less certainty (e.g., a certainty value less than a predetermined threshold). Alternatively or in addition thereto, step 516 may include displaying and/or indicating regions where there is more certainty (e.g., a certainty value greater than a predetermined threshold).

As another example, step 514 may include determining a Gleason score (e.g., for each salient region, for each attribute, for each attribute type, for each co-occurrence, etc.). Step 516 may include visualizing intermediary categories (e.g., indicated by a Gleason score of 3.5 to show an intermediary between a Gleason score of 3 and Gleason score of 4, or an intermediary DCIS grade between intermediate/grade II and high/grade III) in overlapping tissue as a measure of confidence or certainty. Step 516 may include visualizing multiple spatially distinct areas in different combinations, such as a cancerous region and a different and/or non-overlapping non-cancerous region.

Figure 5D:
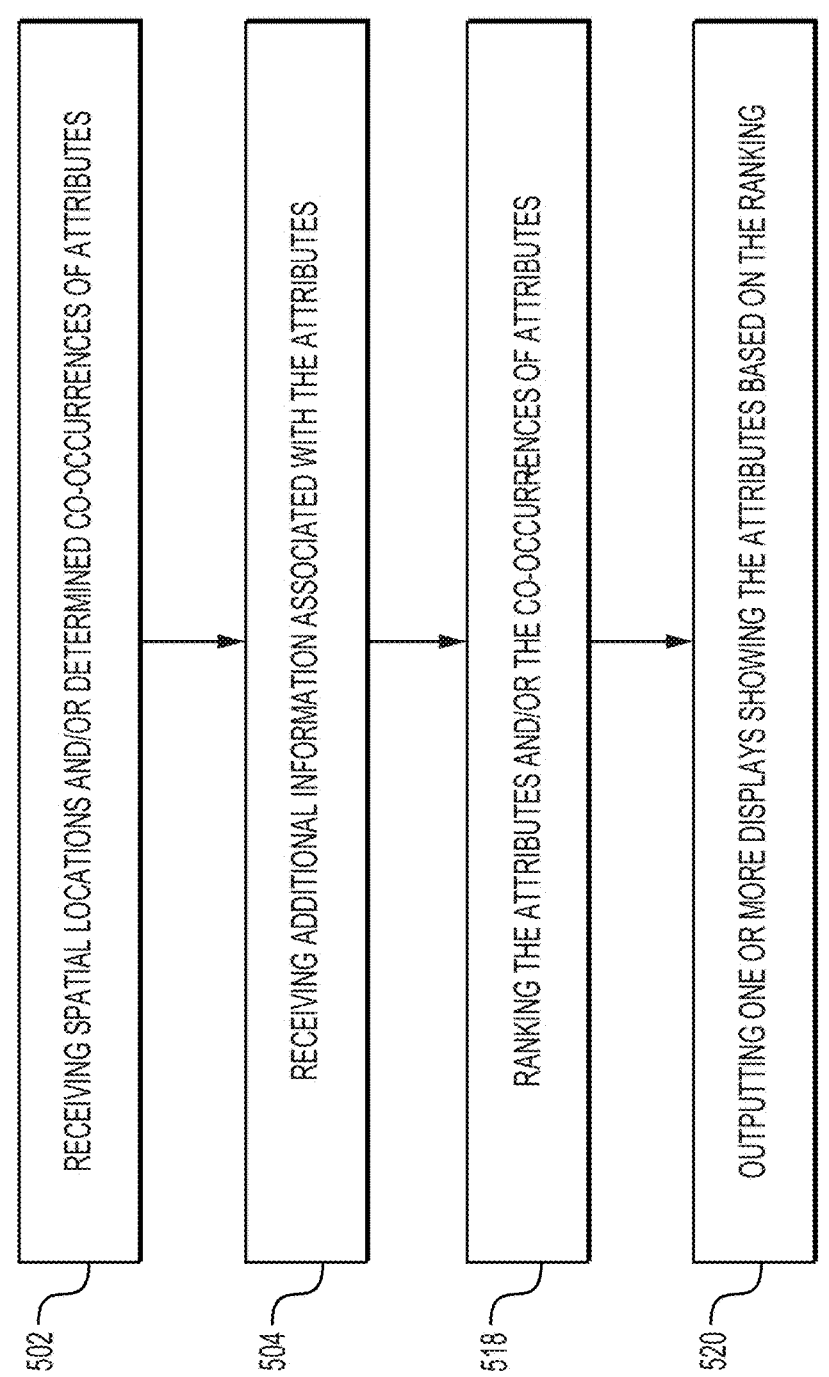
FIG. 5D is a flowchart illustrating an exemplary method for selecting and/or outputting incidents of attributes based on a ranking, according to an example embodiment.

Based on the applied policies (FIG. 5A), determined priority levels (FIG. 5B), and/or determined scores (FIG. 5C), the determined outputs (as determined in steps 508, 512, and/or 516) may determine a list or hierarchy of features, and display those features based on the list. Referring to FIG. 5D, the method 500 may include a step 518 of ranking findings, or the detected attributes and/or co-occurrences.

The list may rank the detected attributes and/or findings (e.g., incidents of co-occurrence) based on the policies (FIG.

5A), priority levels (FIG. 5B), scores (FIG. 5C), and/or based on the detected spatial locations (e.g., more proximate or smaller distances between attributes are ranked higher). The method 500 may include a step 520 of outputting one or more displays showing the attributes based on the ranking.

For example, the AI system, in step 518, may rank incidents of detected co-occurrence of a first attribute and a second attribute highest and rank other areas based on a proximity of the first attribute to the second attribute. In the context of bladder tissue, for example, the AI system, in step 518, may determine to first display incidents of co-occurrence of muscularis propria and cancer and, in step 520, output a display showing regions of the co-occurrence. Where there are multiple incidents of co-occurrence, in step 518, the AI system may rank these incidents in increasing order of proximity based on determined spatial distances between the muscularis propria and cancer. Step 520 may include displaying these incidents in the ranked order so that a pathologist may first view areas or regions where muscularis propria is closest to the cancer.

In some examples, the AI system may, in step 518, determine a display based on a predetermined policy or priority of findings, such as a predetermined ranking where incidents of co-occurrence ranked highest, then incidents of a most relevant attribute or feature (e.g., cancer), and then incidents of a next most relevant attribute or feature (e.g., muscularis propria). Where no incidents of co-occurrence are detected, in step 518, the AI system may determine a display of areas or regions containing just the most relevant attribute or feature (e.g., cancer). Where no incidence of co-occurrence are detected and no incidents of the most relevant attribute are present, in step 518, the AI system may determine a display of areas or regions containing the next most relevant attribute or feature (e.g., muscularis propria). In step 520, the determined attributes to display maybe highlighted, boxed, enlarged or otherwise indicated.

As another example, the AI system, in steps 518 and 520, may determine to first display a first attribute (e.g., invasion, DCIS, tumor) such as in a first screen, to next display a second attribute (e.g., muscle, calcification, edge of tissue) such as in a second screen, and to next display an overlap or co-occurrence of the first and second attributes (e.g., invasion in muscle, calcifications in DCIS, or a proximity or distance from a tumor to a tissue edge) in a third screen. As another example, the AI system may determine a display of a most relevant feature, and, if that most relevant feature is not present or detected, may determine a display of a next most relevant feature, etc.

Based on displayed findings (e.g., according to FIGS. 4, 5A, 5B, 5C, and/or 5D), a pathologist may confirm that one attribute (child and/or dependent attribute) may be derived from a correct related attribute (parent attribute) and/or to verify accuracy of the flagged and/or reported attributes. Many cancers may have descriptive features that might typically be reported (or, according to certain policies or practices, may have to be reported) about the cancer. The pathologist may determine that the attribute and/or feature output (e.g., by the AI system) applies to a correct cancer by reviewing the displays (e.g., in an output tissue map from H&E/IHC stains, such as shown in FIG. 9).

As an example, when in situ and invasive cancer are present on a same digital image, a grade of each cancer may be determined and/or flagged (e.g., based on a score of each attribute determined in step 514 of method 500). A user (e.g., pathologist) may desire to report the grade (e.g., to a patient), so the user may verify, via the displayed outputs, that the output grade corresponds to the correct cancer.

When a user reports a mitotic count for cancer, the pathologist may determine, via the displayed outputs, that a mitoses counted by the AI system are the mitoses found within (and/or overlapping with) the cancer and not outside (or non-overlapping with) the cancer.

Aspects disclosed herein may determine and/or visualize a co-occurrence of different attributes or features to diagnose a disease. Referring to FIG. 6, a method 600 may include a step 602 receiving one or more digital images (e.g., whole slide images or WSIs) from a biopsy or sample into electronic or digital storage (e.g., of an AI system). The method 600 may also include a step 604 of receiving additional information associated with the one or more digital images, such as a sample, tissue, or biopsy type, patient information, etc.

The method 600 may include a step 606 of detecting a presence and location of one or more first incidents of a first attribute or attribute type within the sample. The method 600 may include a step 608 of detecting a presence and location of one or more second incidents of a second attribute or attribute type (e.g., cancer) within the sample.

The method 600 may include a step 610 of comparing the detected locations of the first incidents and the second incidents. For example, step 610 may include determining (e.g., via AI system) whether a distance between a first incident among a plurality of first incidents and a second incident among a plurality of second incidents is less than or equal to a threshold or predetermined distance. Based on the determined distance and/or the comparison, step 610 may include determining whether one of the first or second attributes or features is within a region or area encompassed by the other of the first or second attributes.

The method 600 may include a step 612 of determining a disease state and/or condition based on the comparison. For example, if, in step 610, the AI system determined that the first attribute is within the region or area of the second attribute, then step 612 may include determining that a disease (e.g., cancer invasion) exists and/or an extent of the disease. If, in step 610, the AI system determined multiple instances of co-occurrence, step 612 may include determining whether a disease exists and/or an extent of the disease based on a number of instances of co-occurrence.

The method 600 may include a step 614 of outputting the first and second attributes on a display, such as in a tissue map. Step 614 may include determining which attributes (first incidents of first attribute only, second incidents of second attribute only, incidents of co-occurrences of the first and second attributes, incidents of non-overlap of the first and second attributes) to display and providing indications of co-occurrences, buttons for the user to jump-to certain co-occurrences or attributes based on a determined priority, etc.

Bladder Cancer (in Biopsy)

Technical aspects disclosed herein may be used to determine and visualize co-occurrence of attributes or features to determine or diagnose a bladder cancer condition from a biopsy. Technical aspects disclosed herein may determine a list of hierarchy of features that may be indicative of bladder cancer and/or determining a co-occurrence of those features.

For example, referring to FIG. 7, a method 700 may include a step 702 of receiving an one or more digital images (e.g., whole slide images or WSIs) from a biopsy or sample (e.g., bladder biopsy) into electronic or digital storage (e.g., of an AI system). The method 700 may also include a step 704 of receiving additional information associated with the one or more digital images, such as a tissue or biopsy type, patient information, etc.

The method 700 may include a step 706 of detecting a presence of a predetermined muscle (e.g., detrusor muscle) within the biopsy or sample. The method 700 may also include a step 708 of detecting a presence and location of an invasion (e.g., cancer or bladder cancer). Step 708 may include detecting a presence and location of multiple incidents of an attribute associated with invasion of cancer. The method 700 may include a step 710 of comparing the detected locations of the muscle and the invasion. For example, in step 710, the AI system may determine whether a distance between the detected muscle and the invasion is less than or equal to a threshold distance, whether the invasion is within a region or area encompassed by the detected muscle, a number of co-occurrences of the invasion and the muscle, and/or whether a number of co-occurrences of the muscle and the invasion are greater than a predetermined number of co-occurrences.

The method 700 may include a step 712 of determining a disease (e.g., cancer or bladder cancer) state or extent based on the comparison. For example, if the AI system determines in step 710 that the invasion is within the threshold distance, within the region or area of the detected muscle, and/or that the number of co-occurrences is greater than the predetermined number, then, in step 712, the AI system may determine that a cancer invasion (e.g., bladder cancer invasion) within the muscle (e.g., detrusor muscle) exists and/or determine an extent of the cancer invasion (e.g., proportional to the number of co-occurrences).

The method 700 may include a step 714 of outputting a display of the predetermined muscle and the invasion. In the example of bladder cancer, in step 714, the AI system may determine, based on a priority level or policy (e.g., as discussed with reference to FIGS. 5A-5C), that only co-occurrences or overlapping regions should be displayed, and display a tissue map that indicates the overlapping regions (e.g., such as the display in FIG. 11 showing co-occurrences of a first attribute and a second attribute).

Breast Cancer (in Biopsy)

Technical aspects disclosed herein may be used to determine and visualize co-occurrence of attributes or features to determine or diagnose a breast cancer condition from a biopsy (e.g., incisional biopsy). Technical aspects disclosed herein may determine a list of hierarchy of features that may be indicative of a cancer (e.g., breast cancer or bladder cancer) and/or determining a co-occurrence of those features.

For example, referring to FIG. 8, a method 800 may include a step 802 of receiving one or more digital medical images (e.g., WSIs) from a sample (e.g., biopsy). The method 800 may include a step 804 of receiving additional information associated with the one or more digital images (e.g., biopsy site or location, tissue type, patient information, etc.). The method 800 may include a step 806 of detecting a presence and location of one or more first incidents of a first attribute that indicates an abnormality, such as ductal carcinoma in situ (DCIS), within the sample.

The method 800 may include a step 808 of outputting the presence and location of the one or more first incidents of the first attribute on a display. Step 806 may include determining a grade or severity of the first attribute (e.g., based on a number of occurrences or a proximity of the occurrences), and step 808 may include outputting the severity. Each attribute (e.g., DCIS) may be represented as a binary or probability attribute mask over the tissue, a polygon, etc.

FIG. 9 exemplifies an output as a tissue map 902 showing DCIS on a breast tissue biopsy on a digital image, and a grade of "high." The tissue map 902 may be based on an H&E image or stain and may display and/or indicate overlap with an IHC image or stain. IHC stains may provide biological information related to attributes that may be detected and/or predicted by the AI system. Pathologists may benefit from the ability to visualize the AI attributes derived from H&E stained tissue on the IHC stained tissue, allowing the pathologist to integrate AI data with biological immunohistochemical data.

The tissue map 902 may include other user input features, such as a bar or switch 904 to change an opacity of the detected DCIS. Output locations of the DCIS may have zero or more non-mutually exclusive attributes within the digital image.

Referring back to FIG. 8, the method 800 may include a step 810 of detecting a presence and location of one or more second incidents of a second attribute (e.g., calcification) and a step 812 of outputting the presence and location of the second incidents of the second attribute on the display (e.g., as a subsequent screen or frame, and/or overlaid on the display of the first attribute). Step 810 may include determining a grade or severity of the second attribute (e.g., based on a number of occurrences or a proximity of the occurrences), and step 812 may include outputting the severity. Each attribute (e.g., calcification) may be represented as a binary or probability attribute mask over the tissue, a polygon, etc. FIG. 10 exemplifies an output as a tissue map 1002 of the breast tissue of FIG. 9 showing calcification. The tissue map 1002 may include buttons and/or thumbnails 1004 identifying the detected calcification. A user may select (e.g., click on) one of the buttons 1004 to jump to or zoom in on an attribute or instance corresponding to the selected button 1004.

Referring back to FIG. 8, the method 800 may include a step 814 of comparing the detected locations of the first and second attributes and/or incidents of the attributes, such as DCIS and calcification. For example, in step 814, the AI system may determine whether a distance, area, radius, etc. between an incident of the first attribute and an incident of the second attribute (e.g., DCIS and the calcification) is less than or equal to a threshold distance, area, radius, etc., whether the second attribute (e.g., calcification) is within a region or area encompassed by the first attribute (e.g., DCIS) and/or vice versa, whether an average distance between incidents of the first attribute and incidents of the second attribute is less than or equal to a threshold average, and/or a number of co-occurrences of the first and second attributes. The method 800 may include a step 816 of determining a disease (e.g., cancer) state based on the comparison.

In the example of breast cancer from a biopsy shown in FIGS. 9-10, if, in step 814, the AI system may determine that the calcification is within the region or area of the DCIS and/or overlapping with DCIS, then, in step 816, the AI system may determine that a breast cancer invasion within the tissue exists and/or determine an extent of the breast cancer invasion. As another example, in step 814, the AI system may determine a number of instances of co-occurrence of the DCIS and calcifications, and in step 816, the AI system may determine whether a breast cancer invasion exists and/or an extent of the breast cancer invasion based on (e.g., proportional to) the determined number of instances of co-occurrence.

The method 800 may include a step 818 of outputting and/or displaying, on the display, instances where the first attribute and the second attribute overlap and/or co-occur. This output may be based on the previous outputs to the display and/or shown as a separate screen or frame.

FIG. 11 shows an exemplary output as a tissue map 1102 displaying instances where the DCIS and calcification overlap. Both a DCIS grade and identified areas of calcification may be shown. The tissue map 1102 may include buttons, selectable icons, and/or thumbnails 1104 identifying the overlap instances. A user may select (e.g., click on) one of the buttons 1104 to jump to or zoom in on an overlap instance corresponding to the selected button 1104.

Steps 808, 812, and/or 818 may be performed simultaneously and/or based on a policy or priority (e.g., as discussed with reference to FIGS. 5A through 5C). For example, in steps 808, 812, and/or 818, the AI system may determine to first display the first attribute, to next display the second attribute, and to next display an overlap of the first and second attributes. The AI system may automatically pan or jump between displays (e.g., FIGS. 9, 10, and/or 11), attributes, and/or incidents based on a determined priority. For any one display (e.g., FIG. 11), the AI system may automatically jump and/or zoom to certain co-occurrences or instances of overlap (or, alternatively or in addition thereto, incidents of an individual attribute) based on a determined priority or severity.

Breast Cancer (in Excision)

Technical aspects disclosed herein may be used to determine and visualize co-occurrence of attributes or features to determine or diagnose a breast cancer condition from an excision and/or excisional biopsy. Technical aspects disclosed herein may determine a list of hierarchy of features that may be indicative of breast cancer and/or determining a co-occurrence of those features. Technical aspects disclosed herein may determine a distance to or from margins or features (e.g., edges of tissue) to determine co-occurrence of features.

For example, referring to FIG. 12, a method 1200 may include a step 1202 of receiving one or more digital images (e.g., WSIs) from a sample (e.g., excision) into electronic storage. The method 1200 may include a step 1204 of receiving additional information, such as a tissue type or location, patient information, etc., associated with the one or more digital images into electronic storage. The method 1200 may include a step 1206 of detecting a presence and location of one or more first incidents of a first attribute or feature (e.g., tumor) within the sample. The first attribute may relate to an abnormality of the sample and/or be associated with a disease.

The method 1200 may also include a step 1208 of detecting a presence and location of a margin or edge of a second attribute (e.g., edge of tissue), or other feature relating to a geometry or other aspect of the sample (e.g., excised tissue). The method 1200 may include a step 1210 of comparing the detected locations of the one or more incidents of the first attribute and the edge of the second attribute. For example, in step 1210, the AI system may determine whether a distance between a tumor and an edge of a tissue in an excision is less than or equal to a threshold distance, whether the tumor is within a region or area of interest (e.g., based on the edge of the tissue), and/or a number of co-occurrences.

The method 1200 may include a step 1212 of determining a disease state and/or an extent of the disease based on the comparison. For example, if, in step 1210, the AI system determines that a tumor is within a region or of interest, then, in step 1212, the AI system may determine that a cancer invasion (e.g., breast cancer invasion) within the tissue exists and/or determine an extent or stage of the cancer invasion. If, in step 1210, AI system determines multiple instances of co-occurrence, in step 1212, the AI system may determine whether a breast cancer invasion exists and/or an extent of the breast cancer invasion based on (e.g., proportional to) a determined number of instances of co-occurrence.

The method 1200 may include a step 1214 of outputting the first attribute and/or the edge of the second attribute on a display. As previously described with reference to FIGS. 5A-D and 8-11, the display may include a user interface and/or buttons to pan through findings (e.g., co-occurrences of the first attribute and/or the edge of the second attribute, detected first attribute and/or edge of second attribute, etc.) and/or display findings according to a predetermined policy, priority order, value, or ranking.

Techniques disclosed herein are not limited to bladder cancer and breast cancer. Rather, techniques discussed herein may be used with any type of cancer or disease. For example, techniques describe herein may be used to evaluate prostate cancer. For example, the AI system may determine a presence and/or location of tumor patterns, prostate patterns, and/or Gleason patterns. The AI system may determine or recognize these patterns and determine a combination of all patterns (e.g., as with prostate total tumor detections). The AI system may compare patterns and indicate a confidence level in a recognized pattern.

The AI system may display a tissue map from H&E and display overlap with IHC. IHC stains may provide biological information related to attributes that may be predicted by an AI. Pathologists may benefit from the ability to visualize the AI attribute derived from H&E stained tissue on the IMC stained tissue, allowing the pathologist to integrate AI data with biological immunohistochemical data. Techniques disclosed herein may visualize intermediary categories in overlapping tissue as a measure of confidence.

Techniques disclosed herein may provide reportable features for an interaction of two or more detected attributes. Certain attributes may be found anywhere on an image (e.g., whole slide image) and may be reported and/or flagged by location. Non-cancerous/organic materials may also be found within cancer or a cancerous region and be reported and/or flagged. For example, calcifications within breast cancer and within a benign stroma may be flagged.

Figure 13:
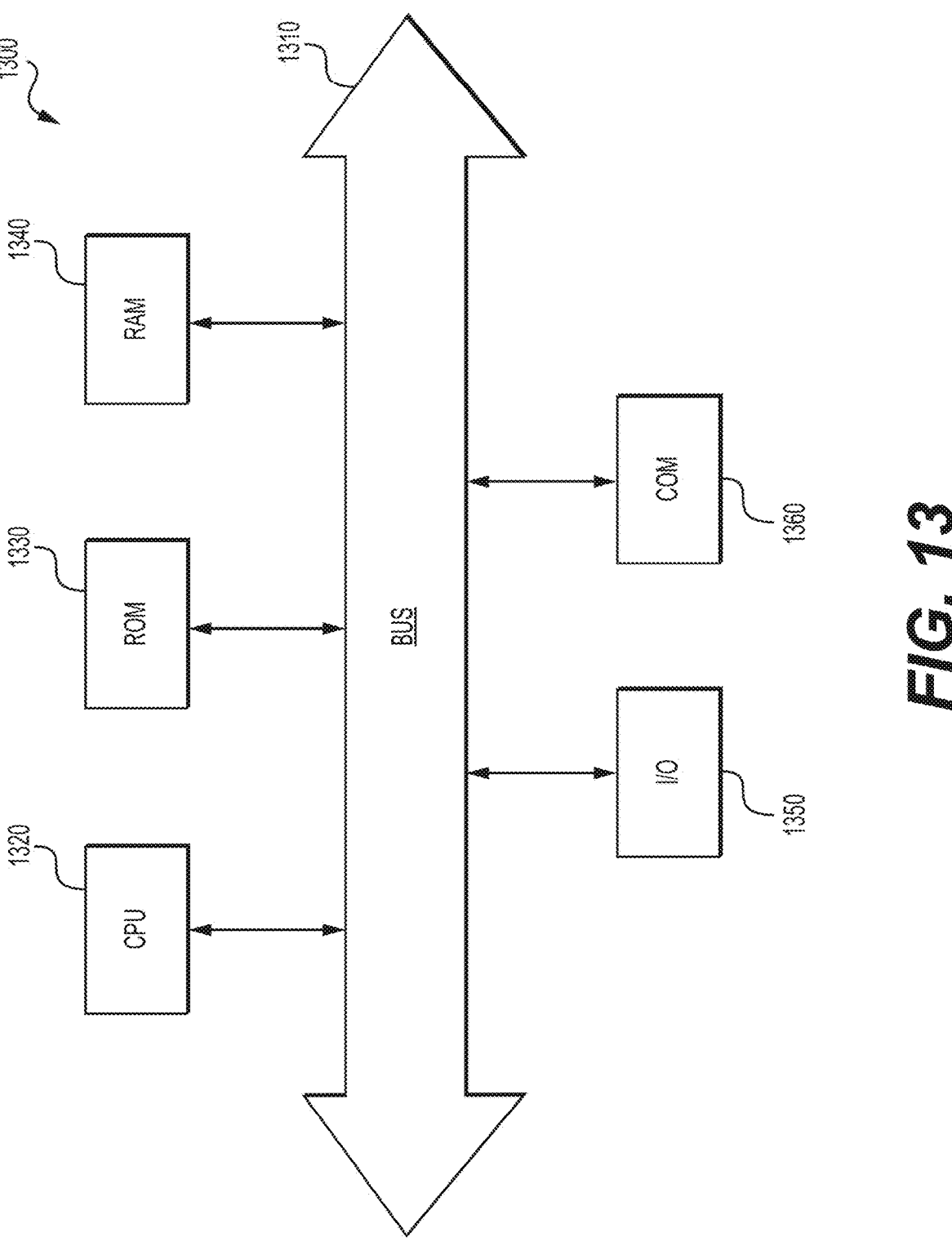
FIG. 13 depicts an example of a computing device that may execute techniques presented herein, according to one or more embodiments.

Referring to FIG. 13, a device 1300 may include a central processing unit (CPU) 1320. CPU 1320 may be any type of processing device including, for example, any type of special purpose or a general-purpose microprocessor device. As will be appreciated by persons skilled in the relevant art, CPU 1320 also may be a single processor in a multi-core/multiprocessor system, such system operating alone, or in a cluster of computing devices operating in a cluster or server farm. CPU 1320 may be connected to a data communication infrastructure 1310, for example a bus, message queue, network, or multi-core message-passing scheme.

Device 1300 may also include a main memory 1340, for example, random access memory (RAM), and may also include a secondary memory 1330. Secondary memory 1330, e.g., a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 1330 may include similar means for allowing computer programs or other instructions to be loaded into device 1300. Examples of such means may include a program cartridge and cartridge interface (such as that found in video game devices), a removable memory chip (such as an EPROM or PROM) and associated socket, and other removable storage units and interfaces, which allow software and data to be transferred from a removable storage unit to device 1300.

Device 1300 also may include a communications interface ("COM") 1360. Communications interface 1360 allows software and data to be transferred between device 1300 and external devices. Communications interface 1360 may include a model, a network interface (such as an Ethernet card), a communications, a PCMCIA slot and card, or the like. Software and data transferred via communications interface 1360 may in the form of signals, which may be electronic, electromagnetic, optical or other signals capable of being received by communications interface 1360. These signals may be provided to communications interface 1360 via a communications path of device 1300, which may be implemented using, for example, wire or cable, fiber optics, a phone line, a cellular phone link, an RF link or other communications channels.

The hardware elements, operating systems, and programming languages of such equipment are conventional in nature, and it is presumed that those skilled in the art are adequately familiar therewith. Device 1300 may also include input and output ports 1350 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Throughout this disclosure, references to components or modules generally refer to items that logically may be grouped together to perform a function or group of related functions. Like reference numerals are generally intended to refer to the same or similar components. Components and/or modules may be implemented in software, hardware, or a combination of software and/or hardware.

The tools, modules, and/or functions described above may be performed by one or more processors. "Storage" type media may include any or all of the tangible memory of the computers, processors or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

The foregoing general description is exemplary and explanatory only, and not restrictive of the disclosure. Other embodiments of the invention may be apparent to those skilled in the art from consideration of the specification and practice of the invention disclosed herein. It is intended that the specification and examples be considered as exemplary only.

What is claimed is:

1. A computer-implemented method for processing electronic medical images, comprising:

receiving one or more digital images of a pathology specimen;

detecting, by applying a first machine learning system, a presence of one or more spatial locations of one or more attributes in the received digital image, the one or more attributes representing one or more tissue types in the one or more digital images, the one or more attributes including a first attribute and a second attribute, the one or more spatial locations including a plurality of first spatial locations of the first attribute and a plurality of second spatial locations of the second attribute;

detecting, by the first machine learning system, a spatial relationship of the one or more spatial locations, the detecting the spatial relationship of the one or more spatial locations including determining a set of relative distances between the plurality of first spatial locations and plurality of second spatial locations;

determining one or more spatial locations of co-occurrence pairs of the first attribute and the second attribute based on the set of relative distances between the plurality of first spatial locations and the plurality of second spatial locations, the co-occurrence indicating a relationship between the first attribute and the second attribute;

determining an extent of disease for the one or more digital images based on a number of instances of the one or more spatial locations of co-occurrence pairs of the first attribute and the second attribute; and outputting, to a display, a visual depiction of the plurality of first spatial locations and the plurality of second spatial locations, the spatial relationship, extent of disease, and the one or more spatial locations of co-occurrence pairs.

2. The method of claim 1, wherein determining the one or more spatial locations of co-occurrence pairs includes selecting specific spatial locations of the plurality of first spatial locations and the plurality of second spatial locations that determined the co-occurrence.

3. The method of claim 1, wherein outputting the visual depiction includes outputting a tissue map that indicates the plurality of first spatial locations and the plurality of second spatial locations of co-occurrence pairs.

4. The method of claim 1, wherein outputting the visual depiction includes outputting a first selectable icon corresponding to the first attribute and a second selectable icon corresponding to the second attribute.

5. The method of claim 1, wherein the method further comprises ranking at least one of:

the plurality of first spatial locations based on a proximity to the plurality of second spatial locations, the plurality of second spatial locations based on a proximity to the plurality of first spatial locations, the spatial locations of co-occurrence pairs, wherein the ranking is based on a predetermined policy that defines a priority of the spatial locations of co-occurrence pairs.

6. The method of claim 1, further comprising detecting that the first attribute has a higher priority than the second attribute.

7. A system for identifying attributes of electronic images and displaying the attributes, the system comprising:

at least one memory storing instructions; and at least one processor configured to execute the instructions to perform operations comprising:

receiving one or more digital images of a pathology specimen;

detecting, by applying a first machine learning system, a presence of one or more spatial locations of one or more attributes in the received digital image, the one or more attributes representing one or more tissue types in the one or more digital images, the one or more attributes including a first attribute and a second attribute, the one or more spatial locations including a plurality of first spatial locations of the first attribute and a plurality of second spatial locations of the second attribute;

detecting, by the first machine learning system, a spatial relationship of the one or more spatial locations, the detecting the spatial relationship of the one or more spatial locations including determining a set of relative distances between the plurality of first spatial locations and plurality of second spatial locations;

determining one or more spatial locations of co-occurrence pairs of the first attribute and the second attribute based on the set of relative distances between the plurality of first spatial locations and the plurality of second spatial locations, the co-occurrence pairs indicating a relationship between the first attribute and the second attribute;

determining an extent of disease for the one or more digital images based on a number of instances of the one or more spatial locations of co-occurrence pairs of the first attribute and the second attribute; and outputting, to a display, a visual depiction of the plurality of first spatial locations and the plurality of second spatial locations, the spatial relationship, extent of disease, and the one or more spatial locations of co-occurrence pairs.

8. The system of claim 7, wherein determining the one or more spatial locations of co-occurrence pairs includes selecting specific spatial locations of the plurality of first spatial locations and the plurality of second spatial locations that determined the co-occurrence.

9. The system of claim 7, wherein outputting the visual depiction includes outputting a tissue map that indicates the plurality of first spatial locations and the plurality of second spatial locations of co-occurrence pairs.

10. The system of claim 7, wherein outputting the visual depiction includes outputting a first selectable icon corresponding to the first attribute and a second selectable icon corresponding to the second attribute.

11. A non-transitory computer-readable medium storing instructions that, when executed by a processor, perform a method for identifying attributes of electronic images and displaying the attributes, the method comprising:

receiving one or more digital images of a pathology specimen;

detecting, by applying a first machine learning system, a presence of one or more spatial locations of one or more attributes in the received digital image, the one or more attributes representing one or more tissue types in the one or more digital images, the one or more attributes including a first attribute and a second attribute, the one or more spatial locations including a plurality of first spatial locations of the first attribute and a plurality of second spatial locations of the second attribute;

detecting, by the first machine learning system, a spatial relationship of the one or more spatial locations, the detecting the spatial relationship of the one or more spatial locations including determining a set of relative distances between the plurality of first spatial locations and plurality of second spatial locations;

determining one or more spatial locations of co-occurrence pairs of the first attribute and the second attribute based on the set of relative distances between the plurality of first spatial locations and the plurality of second spatial locations, the co-occurrence indicating a relationship between the first attribute and the second attribute;

determining an extent of disease for the one or more digital images based on a number of instances of the one or more spatial locations of co-occurrence pairs of the first attribute and the second attribute; and outputting, to a display, a visual depiction of the plurality of first spatial locations and the plurality of second spatial locations, the spatial relationship, extent of disease, and the one or more spatial locations of co-occurrence pairs.

12. The method of claim 1, wherein the one or more attributes include tissue identifying muscularis propria, calcification, or ductal carcinoma in situ.

13. The method of claim 1, wherein the one or more attributes includes a third attribute, the one or more spatial locations including a plurality of third spatial locations of the third attribute.

14. The method of claim 13, further comprising:

determining, by the first machine learning system, a second spatial relationship of the one or more attributes, including determining a second set of relative distances between the plurality of third spatial locations, the plurality of second locations, and the plurality of third locations; and determining, by the first machine learning system, a second one or more locations of co-occurrence pairs between the third attribute and the first attribute based on the set second of relative distances.

15. The method of claim 14, further including:

ranking a priority of the one or more spatial locations of co-occurrence pairs as compared to the second one or more locations of co-occurrence.

16. The method of claim 1, further comprising:

ranking a priority of the one or more spatial locations of co-occurrence pairs;

wherein, the display prioritizes a highest ranked spatial location of co-occurrence pairs by highlighting, boxing, or enlarging the highest ranked spatial location of co-occurrence pair.

17. The system of claim 7, further comprising:

ranking a priority of the one or more spatial locations of co-occurrence pairs;

wherein, the display prioritizes a highest ranked spatial location of co-occurrence pair by highlighting, boxing, or enlarging the highest ranked spatial location of co-occurrence pair.

18. The non-transitory computer-readable medium of claim 11, further comprising:

ranking a priority of the one or more spatial locations of co-occurrence pairs;

wherein, the display prioritizes a highest ranked spatial location of co-occurrence pairs by highlighting, boxing, or enlarging the highest ranked spatial location of co-occurrence pairs.

* * * * *